(12) United States Patent
Felber et al.

(10) Patent No.: US 8,163,542 B2
(45) Date of Patent: Apr. 24, 2012

(54) POTENT COMBINATIONS OF MRNA TRANSPORT ELEMENTS

(75) Inventors: Barbara Felber, Rockville, MD (US); Sergey V. Smulevitch, Frederick, MD (US); George Pavlakis, Rockville, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 16 days.

(21) Appl. No.: 10/557,129

(22) PCT Filed: May 19, 2004

(86) PCT No.: PCT/US2004/015776
§ 371 (c)(1),
(2), (4) Date: Nov. 16, 2005

(87) PCT Pub. No.: WO2004/113547
PCT Pub. Date: Dec. 29, 2004

(65) Prior Publication Data
US 2007/0031921 A1    Feb. 8, 2007

Related U.S. Application Data

(60) Provisional application No. 60/471,988, filed on May 19, 2003, provisional application No. 60/472,223, filed on May 20, 2003.

(51) Int. Cl.
*C12N 15/63* (2006.01)
*C12N 5/07* (2010.01)
*C12P 21/00* (2006.01)

(52) U.S. Cl. ............ 435/320.1; 435/325; 435/69.1

(58) Field of Classification Search .................. None
See application file for complete search history.

(56) References Cited

U.S. PATENT DOCUMENTS 5,585,263 A  12/1996 Hammarskjold
5,880,276 A   3/1999 Hammarskjold et al.
6,365,150 B1 *  4/2002 Leboulch et al. ............ 424/93.2

FOREIGN PATENT DOCUMENTS

WO    WO 99/61596 A2    12/1999

OTHER PUBLICATIONS

Bray, Molly et al.; "A small element from the Mason-Pfizer monkey virus genome makes human immunodeficiency type 1 expression and replication Rev-independent"; Biochemistry; *Proc. Natl. Acad. Sci. USA*; Feb. 1994; pp. 1256-1260; vol. 91.
Ernst, Robert K. et al.; "A Structured Retroviral RNA Element That Mediates Nucleocytoplasmic Export of Intron-Containing RNA"; *Molecular and Cellular Biology*; Jan. 1997; pp. 135-144; vol. 17, No. 1; American Society for Microbiology.
Grüter, Patric et al.; "TAP, the Human Homolog of Mex67p, Mediates CTE-Dependent RNA Export from the Nucleus"; *Molecular Cell*; Apr. 1998; pp. 649-659; vol. 1; Cell Press.
Nappi, Filomena et al.; Identification of a Novel Posttranscriptional Regulatory Element by Using a *rev*- and RRE-Mutated Human Immunodeficiency Virus Type 1 DNA Proviral Clone as a Molecular Trap; *Journal of Virology*; May 2001; p. 4558-4569; American Society for Microbiology.
Tabernero, Carlos et al.; "The Posttranscriptional Control Element of the Simian Retrovirus Type 1 Forms an Extensive RNA Secondary Structure Necessary for Its Function"; *Journal of Virology*; Sep. 1996; pp. 5998-6011; American Society for Microbiology.
Tabernero, Carlos et al.; "Identification of an RNA Sequence within an Intracisternal-A Particle Element Able to Replace Rev-Mediated Posttranscriptional Regulation of Human Immunodeficiency Virus Type 1"; *Journal of Virology*; Jan. 1997; pp. 95-101; vol. 71, No. 1.
Valentin, Antonio, et al.; "Reduced Viral Load and Lack of CD4 Depletion in SCID-hu Mice Infected with Rev-Independent Clones of Human Immunodeficiency Virus Type 1"; *Journal of Virology*; Dec. 1997; pp. 9817-9822; vol. 71. No. 12; American Society for Microbiology.
Von Gegerfelt, Agneta and Barbara K. Felber; "Replacement of Post-transcriptional Regulation in SIVmac239 GEnerated a Rev-Independent Infectious Virus Able to Propagate in Rhesus Peripheral Blood Mononuclear Cells" *Virology*; 1997; pp. 291-299; vol. 232; Academic Press.
Von Gegerfelt, Agneta et al.; "Persistent Infection of Rhesus Macaques by the Rev-Independent Nef(—) Simian Immunodeficiency Virus SIVmac239: Replication Kinetics and Genomic Stability"; *Journal of Virology*; Jul. 1999; pp. 6152-6165; vol. 73, No. 7; American Society for Microbiology.
Von Gegerfelt, Agneta et al.; "Rev-Independent Simian Immunodeficiency Virus Strains Are Nonpathogenic in Neonatal Macaques" *Journal of Virology*; Jan. 2002; pp. 96-104; vol. 76, No. 1; American Society for Microbiology.
Wodrich, Harald et al.; "Multiple copies of the Mason-Pfizer monkey virus constitutive RNA transport element lead to enhanced HIV-1 Gag expression in a context-dependent manner"; *Nucleic Acids Research*; 2000; pp. 901-910; vol. 28, No. 4; Oxford University Press.
Wodrich, Harald et al.; "A New RNA Element Located in the Coding Region of a Murine Endogenous Retrovirus Can Functionally Replace the Rev/Rev-Responsive Element System in Human Immunodeficiency Virus Type 1 Gag Expression"; *Journal of Virology*; Nov. 2001; pp. 10670-10682; vol. 75, No. 22; American Society for Microbiology.
Zolotukhin, Andrei S. et al.; "Continuous Propagation of RRE(—) and Rev(—)RRE(—) Human Immunodeficiency Virus Type 1 Molecular Clones Containing a *cis*-Acting Element of Simian Retrovirus Type 1 in Human Peripheral Blood Lymphocytes"; *Journal of Virology*, Dec. 1994; pp. 7944-7952; vol. 68, No. 12; American Society for Microbiology.

* cited by examiner

*Primary Examiner* — Michael Burkhart
(74) *Attorney, Agent, or Firm* — Kilpatrick Townsend & Stockton LLP

(57) ABSTRACT

This invention provides expression vectors that comprise a combination of RNA transport elements that improve expression.

29 Claims, 19 Drawing Sheets

Figure 2

```
RTEwt  :   1  ccgtggggtgcgaggctaagcactgcacagaggatagcttgctgttggcatcctgtggaa   60
              ||||||||||||||||||||||||||||||||||||||||||||||||||||||||||||
RTEM26 :   1  ccgtggggtgcgaggctaagcactgcacagaggatagcttgctgttggcatcctgtggaa   60

RTEwt  :  61  ggcacgtctgattgcatgaaggttcagtgtcctagttccccttccccccaggaaaacgaca  120
              ||||||||||||||||||||||||||||||||||||||||||||||||||||||||||||
RTEM26 :  61  ggcacgtctgattgcatgaaggttcagtgtcctagttccccttccccccaggaaaacgaca  120

RTEwt  : 121  cgggagctggccaagacctctctgggtgatgagcctaagggatggttttgtgtagggccc  180
              ||||||||||||||||||||||||||||||||||||||||||||||||||||||||||||
RTEM26 : 121  cgggagctggccaagacctctctgggtgatgagcctaagggatggttttgtgtagggccc  180

RETwt  : 181  ctatgcttgcacactggggctgggggatcagacctctaccttcacccatgagg  226
              ||||||||||||||||||||||||||||||||||||||||||||||||||||
RTEM26 : 181  ctatgcttggcggctgggggatcagacctctaccttcacccatgagg  226
```

Figure 5

```
RTEM26 1-226
  1  CCGTGGGGTG CGAGGCTAAAG CACTGCACAG AGGATAAGCTT GCTGTTGGCA

51  TCCTGTGGAA GGCACGTCTG ATTGCATGAA GGTTCAGTGT CCTAGTTCCC

101  TTCCCCCAGG AAAAACGACA CGGGGAGCTGG CCAAGACCTC TCTGGGTGAT

151  GAGCCTAAGG GATGGTTTTG TGTAGGGCCC CTANGCTTGg cggCTGGGGA

SacII        BamHI  XbaI
                         spacer 28 nt  tatcgatacegcgggggtcctctggagt

201  TCAGACCTCT ACCTTCACCC ATGAAGG

CTE 1-173
255  AGACCACCTC CCCTGCGAGC TAAGCTGGAC AGCCAATGAC GGGTAAGAGA

305  GTGACATTTT TCACTAACCT AAGACAGGAG GGCCGTCAGA GCTACTGCCT

355  AATCCAAAGA CGGGTAAAAG TGATAAAAAT GTATCACTCC AACCTAAGAC

405  AGGCGCAGCT TCCGAGGGAT TTG
```

```
                       1                                                              62
consensus A (RTE)     CCGTGGGCTGCGAGGCTATGCATGCACAAGAGGATAGGTTGTATGCTGTTGGCATTCCTGTCGAAGG
consensus B              k  a        t   a                t                a  tt  c          g
consensus C              ga a  a     c   a          gtag agr c ctgcg g  twataga c tattcta     g   a a
consensus D              ga a  a                    atggta a c ctgcg g  vatca tga c atatcca   g   a a
                                                            SL I                    SL II 63                                                                              131
consensus A (RTE)     CAYGTCTGATTGCATGAAGCTTCCTGTAGTTGCTTCCCCCAGGAAAAAACGACACGGGAGCTGG
consensus B                                                                         g
consensus C              atc  t         a                        gt        ca  g                       a
consensus D              atc  t         t                        gt        ca  gc                  c a a
                                                    SL III 132                                                                             194
consensus A (RTE)     CCAAGACCTCCTGTGGGTCAATGAGCCTTAAGGGATGTTTTGTGTAGGCCCCTATGCT TGCAC
consensus B              t  g gttr          aaayctg              a tcaa cc   ac t       yw
consensus C              t  g g             g                    gg a ga  a     c  t      tacc
consensus D              t  g gttg          g aag tcg            a c  aa cc   ac t        tacc a
                                                    SL IV 195                                                  226
consensus A (RTE)     ACTGGGGATCAGACCTCTACCTTCACCCATGAGG
consensus B              tt                                  ga
consensus C              tt                 t  c      t   tcatta
consensus D                                 t  c      t   tcatta Figure 15B
```

```
        1                                                              62
RTE       CCGTGGGGTGCCTASCCTAAGGACTGCAGAGGATAGCTGCTCTTGGCATCCTGTGTGGAAGG
AL607146  ga  a  a     at  tg       g                  ga tcc a          a
AC079845  ga  a  a     a   t        g                  ga tcc a g        a
AL450331  ga  a  a     at  t        g                  ga tct a g        a
                           SL I                         SL II 63                                                             131
RTE       CACGTCTCGATTGCATGAAGGTTCACTGTCTCAGGCGCTTGCCCCAGG AAAAACGACACGGGAGCTGGC
AL607146  a   gat           g    g   g       c           t  a       g         a  t
AC079845  t   atc   t       a    a   g       c              c             c a a  a
AL450331  t   atc   t       a    a   g       c                            c a a  t
                            SL III 132                                                            194
RTE       CAAGACCTCTCTGTGGGTGATCAGCCTAAGGGGATGGTTTGTGTAGGGCCCCTATGCTTGCACAC
AL607146  g gttg              aagcctg      a c aa cc  ac t          ttc
AC079845  g c                 a            gg a ga    a  c    t   t t a c a
AL450331  g gttg              aagcctg      a c aa cc  ac t    t   t t a c a
                              SL IV 195                        226
RTE       TGGGGATCAGACCTCTACCTTCACCCCATGAGG
AL607146  a            tc       t    t  aa
AC079845               tt       t c  c    t tcatta
AL450331               tt       t t  c    t tcatta
```

Figure 15C

POTENT COMBINATIONS OF MRNA TRANSPORT ELEMENTS

CROSS-REFERENCE TO RELATED APPLICATIONS

This application claims the benefit of U.S. provisional application Nos. 60/471,988, filed May 19, 2003, and 60/472,223, filed May 20, 2003, each of which applications is herein incorporated by reference.

BACKGROUND OF THE INVENTION

Efficient transport of the mRNA is an important step for achieving efficient expression. RNA transport is controlled by a complex interaction of cellular proteins with the mRNAs in the nucleus, leading to cytoplasmic export and expression. Two types of potent retroviral RNA transport elements have been identified. The constitutive transport element (CTE) is essential for the nucleo-cytoplasmic export of unspliced RNA of the simian type D retroviruses. (Bray, et al., *Proc Natl Acad Sci USA* 91:1256-1260, 1994; Tabernero, et al., *J Virol* 71:95-101, 1997; Tabernero, et al., *J Virol* 70:5998-6011, 1996). A related element was identified in a subclass of rodent intracisternal A particle retroelements (Tabernero, et al., *J Virol* 71:95-101, 1997). The RNA transport element (RTE) is present in another subset of rodent intracisternal A particle retroelements (Nappi, et al., *J Virol* 75:4558-69 2001). The primary sequence of these elements are distinct. It has been demonstrated that both CTE and RTE are posttranscriptional control elements promoting expression of otherwise poorly expressed mRNAs such as gag and env from a mutant HIV lacking the viral Rev-RRE control mechanism (Nappi, et al., *J Virol* 75:4558-69 2001; Valentin, et al., *J Virol* 71:9817-9822, 1997; von Gegerfelt & Felber. *Virology* 232:291-299, 1997)

CTEs and RTEs are RNA binding sites for distinct cellular factors mediating the export of CTE- and RTE-containing mRNAs. RTEs and CTEs fold into distinct extended RNA stem-loop structures. Both CTEs and RTEs function in cells of different species, indicating conserved cellular export mechanisms. While the cellular TAP/NXF1 has been identified to be the CTE export factor (Grüter, et al., *Mol Cell* 1:649-659, 1998) the cellular factor promoting RTE export is still unknown. TAP/NXF1 does not bind RTE (Nappi, et al., *J Virol* 75:4558-692001). However, using a microinjected *Xenopus* oocyte RNA transport assay, it was found that CTE RNA can compete for RTE export, indicating, that TAP/NXF1 is involved in RTE RNA export. Not to be bound by theory, the current working model implies another factor interacting with RTE and acting as adapter to link RTE to the export receptor TAP/NXF1.

As noted above, an important step in achieving efficient expression in eukaryots is RNA transport. The role of CTEs and RTEs in RNA transport has been studied individually. The presence of more than one copy of CTE in some, but not all, cases has shown increases in expression relative to one copy of CTE alone (Wodrich et al *Nucl Acid Res* 28:901-910, 2000). However, the effects of the combination of CTE and RTE have not been evaluated.

This invention provides a novel tool to improve expression of unstable mRNAs. The invention provides a modified RTE element that functions better than the wildtype element. Moreover, the invention provides vectors comprising a combination of an RTE, e.g., the mutant RTE, and a CTE, which combination enhances gene expression. Since the function of these elements is conserved in mammalian cells, the use of the invention (RTE-CTE combination of RNA export elements) provides a simple method to improve gene expression to levels otherwise only achieved via more cumbersome RNA optimization.

In addition, the combination RTE/CTE has an added advantage in that it does not duplicate sequences, as is the case of vectors having multiple CTEs. This can be important, as the vectors are typically grown in bacteria and sequence duplication is often not well tolerated in many bacterial systems.

This invention thus provides vectors and methods of using the vectors to obtain high level expression of genes, including for applications such as gene therapy. Further, the RTE/CTE combination can be used in any gene transfer scenario where genes may be poorly expressed, e.g., DNA-based cytokine or viral antigen vaccine vectors. This applies to the field of retroviral vector development, the development of DNA-based vaccine vectors and other applications to enhance gene expression.

BRIEF SUMMARY OF THE INVENTION

The invention provides two RNA transport elements that in combination enhance expression of a transcript that comprises the two transport elements. These elements are the constitutive transport element (CTE), which is important for the nucleo-cytoplasmic export of the unspliced RNA of the simian type D retroviruses. The other element is the RNA transport element, RTE, which is present in a subset of rodent intracisternal A particle retroelements.

In one aspect, the invention provides a vector, e.g. a lentiviral vector, retroviral vector, adenoviral vector, adeno-associated viral vector, or plasmid, comprising an expression cassette encoding a transcript that comprises a RTE and a CTE, wherein the presence of the RTE and CTE increases expression of the transcript. In typical embodiments, the RTE is an RTEM26. For example, the RETM26 can comprise the sequence set forth in SEQ ID NO:2. In one embodiment, the RTEM26 and the CTE are positioned in the 3' untranslated region of a transcript encoded by the expression cassette. Often, the RTE and the CTE are separated by 100 nucleotides or less. In some embodiments, the RTE and the CTE are separated by 30 nucleotides or less. In one embodiment, the RTE and the CTE are comprised by the sequence set forth in SEQ ID NO:3. The expression cassette can comprise a sequence encoding a viral gene product, for example, a retroviral gene product such as an HIV-1 gag or HIV-1 env.

In another aspect, the invention provides a vector comprising an expression cassette encoding a transcript that comprises an RTEM26.

The invention also provides methods of using the vectors to enhance expression of a gene product of interest.

BRIEF DESCRIPTION OF THE DRAWINGS

FIG. 2 shows a comparison of wildtype RTE (SEQ ID NO:1) and a mutant RTE (RTEM26) (SEQ ID NO:2).

FIG. 5 shows the sequence of RTEM26-CTE (SEQ ID NO:3).

FIG. 10A provides a schematic of the expression vector. The env cDNA is expressed from HIV-1 LTR promoter (Schwartz et al *J Virol.* 64: 5448-5456, 1990) FIG. 10B shows the results of a Western blot analysis of the levels of expressed env protein. The lanes show the level of expressed env protein from env cDNA clone pNL1.5E containing the indicated RNA export elements. The results show that RTEM26-CTE mediates enhanced expression of HIV-1 env.

FIG. 11A provides a schematic of the Rev(−)RRE(−)ΔnefCTE(+)SIVmac239 clone (Von Gegerfelt et al. *Virology* 232:291-299, 1997; *J Virol.* 73:6159-6165, 1999; *J Virol.* 76:96-104, 2002) into which RTEM26 was cloned. FIG. 11A shows the generation of Rev-independent molecular clones of SIVmac239 containing the RTEm26CTE RNA export element. FIG. 11B provides data showing the expression of the plasmid in 293 cells. The results show that RTEm26CTE mediates increased expression from molecular clone SIV R-R-Δnef FIG. 12 provides exemplary data showing that the position of the individual elements within the RTE/CTE combination is interchangeable.

FIG. 15B shows the alignment of the consensus of each family (SEQ ID NOS:7-10). FIG. 15C shows the alignment of the four prototype family members (SEQ ID NOS:1 and 11-13).

DETAILED DESCRIPTION OF THE INVENTION

Definitions

The term "RTE" refers to a post-transcriptional regulatory element that is a cis-acting nucleic acid sequences involved in the transport, stability, and translation of RNA transcripts. Exemplary RTE sequences are provided in WO 99/61596. RTE folds into an extended RNA stem-loop structure. RTE sequences for use in the invention have at least 60% identity, often 70%, 80%, 85%, 90%, 95%, or greater identity, as determined with reference to the cores sequence shown in SEQ ID NO:1.

Figure 1:
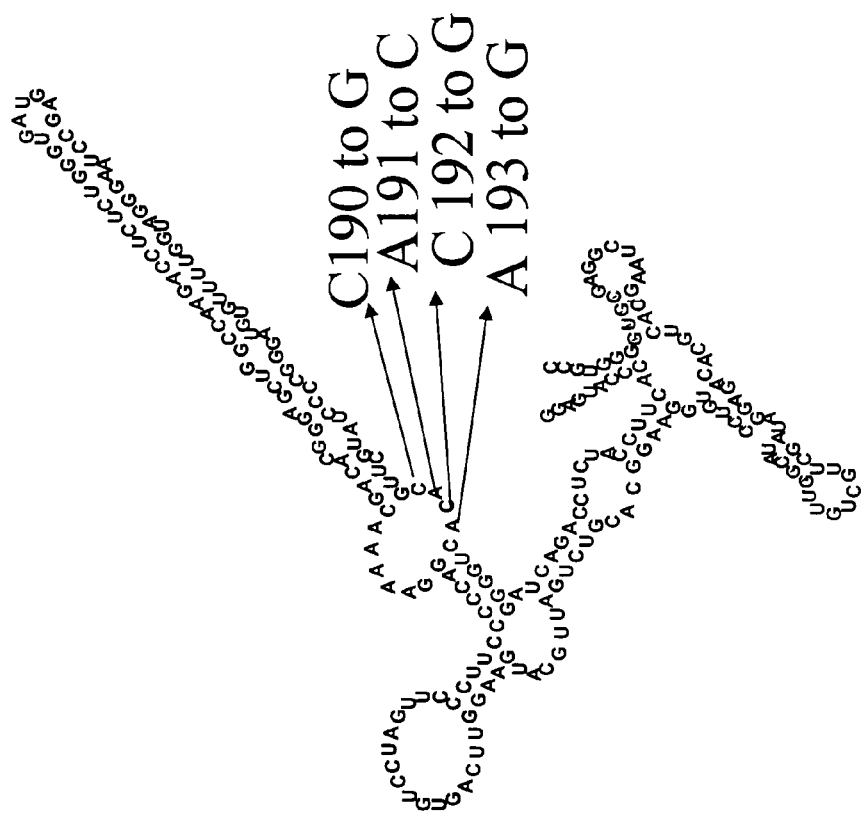
FIG. 1 shows the modeled structure and sequence of RTEM26 (SEQ ID NO:5).

An "RTEM26" as used herein refers to an RTE that comprises four nucleotide substitutions at the positions indicated in FIG. 1. An RTEM26 has at least 60% identity, often 70%, 80%, 85%, 90%, 95%, or greater identity, as determined with reference to the core sequence shown in SEQ ID NO:2.

The term "CTE" refers to a cis-acting constitutive transport element that functions in RNA transport. Exemplary CTE sequences are provided, e.g., in Tabernero, et al., *J Virol.* 70:5998-6011, 1996; and U.S. Pat. Nos. 5,880,276 and 5,585,263. CTE sequences for use in the invention have at least 60% identity, often 70%, 80%, 85%, 90%, 95%, or greater identity, as determined with reference to the exemplary sequence SEQ ID NO:4.

"Enhanced expression" in the context of this invention refers to increased expression relative to a control. An increase in expression is achieved when the value relative to the control is 110%, more preferably 150%, more preferably 200-500% (i.e., two to five fold higher relative to the control), more preferably 1000-3000% higher.

The term "HIV" refers to a lentivirus usually called "human immunodeficiency virus" which is believed to the causal agent of acquired immune deficiency syndrome, or AIDS. There are several known subtypes of HIV, including HIV-1 and HIV-2. HIV and AIDS are well described in the literature and, e.g., are further described by Gottfredsson (1997) *Front Biosci.* 2: D619-D634; Burton (1997) *Proc. Natl. Acad. Sci. USA* 94:10018-10023; Barnadas (1997) *J Cutan. Pathol.* 24:507-510; Doms (1997) *Virology* 235:179-190; Cossarizza (1997)*AIDS* 11:1075-1088; Carpenter (1997) *JAMA* 277:1962-1969; Klein (1995) *Trends Microbiol.* 3:386-391.

The term "Wild-type" refers to any form (e.g., tertiary structure), structure (e.g., secondary structure) or sequence (e.g., primary structure) of a composition, e.g., a nucleic acid, as found in nature, versus structures or sequences that have been manipulated by man.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The term "expression cassette" refers to any recombinant expression system for the purpose of expressing a nucleic acid sequence of the invention in vitro or in vivo, constitutively or inducibly, in any cell, including prokaryotic, yeast, fungal, plant, insect or mammalian cell. The term includes linear or circular expression systems. The term includes expression systems that remain episomal or integrate into the host cell genome. The expression systems can have the ability to self-replicate or not, i.e., drive only transient expression in a cell. The term includes recombinant expression cassettes which contain only the minimum elements needed for transcription of the recombinant nucleic acid. The term also includes expression vectors. The mutant RTE and RTE/CTE combination sequences can be incorporated into any eukaryotic expression system, typically mammalian expression systems, to improve expression of unstable RNAs.

The term "isolated," when referring to a molecule or composition, such as, for example, a polypeptide or nucleic acid, means that the molecule or composition is separated from at least one other compound, such as a protein, other nucleic acids (e.g., RNAs), or other contaminants with which it is associated in vivo or in its naturally occurring state. Thus, a polypeptide or nucleic acid is considered isolated when it has been isolated from any other component with which it is naturally associated, e.g., cell membrane, as in a cell extract. An isolated composition can, however, also be substantially pure. An isolated composition can be in a homogeneous state and can be in a dry or an aqueous solution. Purity and homogeneity can be determined, for example, using analytical chemistry techniques such as polyacrylamide gel electrophoresis (SDS-PAGE) or high performance liquid chromatography (HPLC).

The term "polynucleotide," "nucleic acid molecule" or "nucleic acid sequence" refers to a deoxyribonucleotide or ribonucleotide oligonucleotide in either single- or double-stranded form. The term encompasses nucleic acids, i.e., oligonucleotides, containing known analogues of natural nucleotides which have similar or improved binding properties, for the purposes desired, as the reference nucleic acid. The term also includes nucleic acids which are metabolized in a manner similar to naturally occurring nucleotides or at rates that are improved thereover for the purposes desired. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs, which contain non-ionic backbones, such as N-(2-aminoethyl) glycine units); see Oligonucleotides and Analogues, A Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) *J. Med. Chem.* 36:1923-1937; Antisense Research and Applications (1993, CRC Press) in its entirety and specifically Chapter 15, by Sanghvi. Phosphorothioate linkages are described in WO 97/03211; WO 96/39154; Mata (1997) *Toxicol Appl Pharmacol* 144:189-197. Other synthetic backbones encompasses by the term include methylphosphonate linkages or alternating methylphosphonate and phosphodiester linkages (Strauss-Soukup (1997) *Biochemistry* 36:8692-8698), and benzylphosphonate linkages (Samstag (1996) *Antisense Nucleic Acid Drug Dev.* 6:153-156). The term nucleic acid is used interchangeably with gene, DNA, cDNA, RNA, mRNA, oligonucleotide primer, probe and amplification product.

The term "exogenous" as in "exogenous nucleic acid" refers to a molecule (e.g., nucleic acid or polypeptide) that has been isolated, synthesized, and/or cloned, in a manner that is not found in nature, and/or introduced into and/or expressed in a cell or cellular environment other than or at levels or forms different than the cell or cellular environment in which said nucleic acid or protein can be found in nature. The term encompasses both nucleic acids originally obtained from a different organism or cell type than the cell type in which it is expressed, and also nucleic acids that are obtained from the same organism, cell, or cell line as the cell or organism in which it is expressed.

The term "endogenous" refers to a molecule, e.g., a nucleic acid or polypeptide, in a form, structure and/or sequence found in nature.

"Sequence identity" in the context of two nucleic acid sequences includes reference to the nucleotides in the two sequences that are the same when aligned for maximum correspondence over a specified "comparison window." Sequence identity analysis is used to determine whether a nucleic acid is within scope of the invention. "Sequence identity" can be analyzed by optimal alignment of sequences for comparison using any means to analyze sequence identity (homology) known in the art, e.g., by the progressive alignment method of termed "PILEUP"; by the local homology algorithm of Smith & Waterman (1981) *Adv. Appl. Math.* 2:482; by the homology alignment algorithm of Needleman & Wunsch (1970) *J. Mol. Biol.* 48:443; by the search for similarity method of Pearson (1988) *Proc. Natl. Acad. Sci. USA* 85:2444; by computerized implementations of these algorithms, e.g. BLAST, GAP, BESTFIT, FASTA, and TFASTA in, e.g., the Wisconsin Genetics Software Package, Genetics Computer Group, 575 Science Dr., Madison, Wis.; or, by inspection. See also Morrison (1997) *Mol. Biol. Evol.* 14:428-441, as an example of the use of PileUp, ClustalW, TreeAlign, MALIGN, and SAM sequence alignment computer programs. PILEUP uses a simplification of the progressive alignment method of Feng & Doolittle (1987) *J. Mol. Evol.* 35:351-360, and is similar to the method described by Higgins & Sharp (1989) *CABIOS* 5:151-153. The BLAST algorithm is described in Altschul (1990) *J. Mol. Biol.* 215:403-410, and BLAST software for analyses is publicly available, e.g., see National Center for Biotechnology Information at http://www.ncbi.nlm.nih.gov/. See also Corpet (1988) *Nucleic Acids Res.* 16:10881-90; Huang (1992) *Computer Applications in the Biosciences* 8:155-65; Pearson (1994) *Methods in Molec. Biol.* 24:307-31. For purposes of this application, the percent identity can be determined using the default parameters of BLAST 2.0 without the filter. "Determined with reference" in this context means that the sequences are determined when aligned for maximal correspondence over the reference sequence.

The term "recombinant," when used with reference to, e.g., a cell, nucleic acid, polypeptide, expression cassette or vector, refers to a material, or a material corresponding to the natural or native form of the material, that has been modified by the introduction of a new moiety or alteration of an existing moiety, or is identical thereto but produced or derived from synthetic materials. For example, recombinant cells express genes that are not found within the native (non-recombinant) form of the cell (i.e., "exogenous nucleic acids") or express native genes that are otherwise expressed at a different level, typically, under-expressed or not expressed at all. The term "recombinant means" refers to techniques where, e.g., a recombinant nucleic acid such as a cDNA encoding a protein or an antisense sequence, is inserted into an expression cassette, such as an expression vector, the resultant construct is introduced into a cell, and the cell expresses the nucleic acid, and the protein, if appropriate. "Recombinant means" also encompass the ligation of nucleic acids to coding or promoter sequences from different sources into one expression cassette or vector for expression of a fusion protein, constitutive expression of a protein, or inducible expression of a protein.

The term "motif" or "domain" refers to a nucleic acid sequence pattern or structure, which is shared between related molecules.

The term "ameliorating" or "ameliorate" refers to any indicia of success in the treatment of a pathology or condition, including any objective or subjective parameter such as abatement, remission or diminishing of symptoms or an improvement in a patient's physical or mental well-being. Amelioration of symptoms can be based on objective or subjective parameters; including the results of a physical examination and/or a psychiatric evaluation.

The term "vaccine" is used in its ordinary sense, meaning an agent which is capable of eliciting a humoral and/or cell-mediated immunoprotective immune response when administered to an individual with an at least partially functioning immune system.

The term "prophylaxis" refers to any form of prevention, delay or abatement a pathology or condition or symptom thereof, including any objective or subjective parameter.

DETAILED DESCRIPTION

This invention relies on routine techniques in the field of recombinant genetics. Basic texts disclosing the general methods of use in this invention include Sambrook et al., *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994-April 2004 update).

The invention provides for methods and reagents for using the RTE-CTE combination in various expression vectors to improve expression levels in cells, e.g. in eukaryotic cells such as mammalian cells. The construction of such expression vectors are well known in the art. Expression constructs contain various elements to mediate expression of a transcript encoded by a gene of interest. These elements include regulatory elements, e.g., promoters and/or enhancers linked to the sequences to be expressed. Such sequences are well known and include both constitutive and inducible or tissue-specific promoters.

Expression constructs typically contain at least one independent terminator sequence, other sequences to optimize expression, e.g., IRES, splice donor and splice acceptor sites, polyadenylation sequences, sequences permitting replication of the cassette in eukaryotes, or prokaryotes, or both, (e.g., shuttle vectors) and selection markers for both prokaryotic and eukaryotic systems. These components are also well known. Further, kits for many such expression systems are commercially available.

RTE Sequences

RTE sequences that are used in the invention include naturally occurring RTEs and variants that retain their function. RTE sequences can be determined with reference to either the wildtype RTE sequence or RTEM26 sequence shown in FIGS. 1 and 2. The RTE contains four stem-loops that are typically required for function in mammalian cells. Only part of the element is needed to mediate RNA transport in non-mammalian cells, e.g., *Xenopus*. RTE sequences are known in the art, e.g., WO 99/61596 and Nappi, et al., *J Virol* 75:4558-69 2001).

The RTEs of the invention often comprise mutations at any one of the 4 positions indicated in FIGS. 1 and 2 (190, 191, 192, and 193). These substitutions may be the particular substitutions shown in FIG. 2, or may be substitutions with nucleotide or nucleotide analogs that result in the same activity. In some embodiments, the RTE comprises at least two or at least three of the mutations shown in FIG. 2. In a preferred embodiment, a variant RTE that comprises all four of the mutations shown in the RTEM226 sequence of FIG. 1 and FIG. 2 is used in the invention.

The invention includes the use of variant RTE sequences that differ from the wildtype RTE at positions outside of the 4 positions shown in FIGS. 1 and 2. Such variant sequences maintain the stem-loop structure and typically have at least 200 contiguous nucleotides of the wt RTE and RTEM26 sequence shown in FIG. 2. For example, variants can comprise nucleotide substitutions at positions that participate in a nucleotide-nucleotide binding interaction, e.g., positions shown in FIG. 1. In such cases, the variant also typically comprises a compensatory substitution such that the structure of the RTE is retained.

Figure 14:
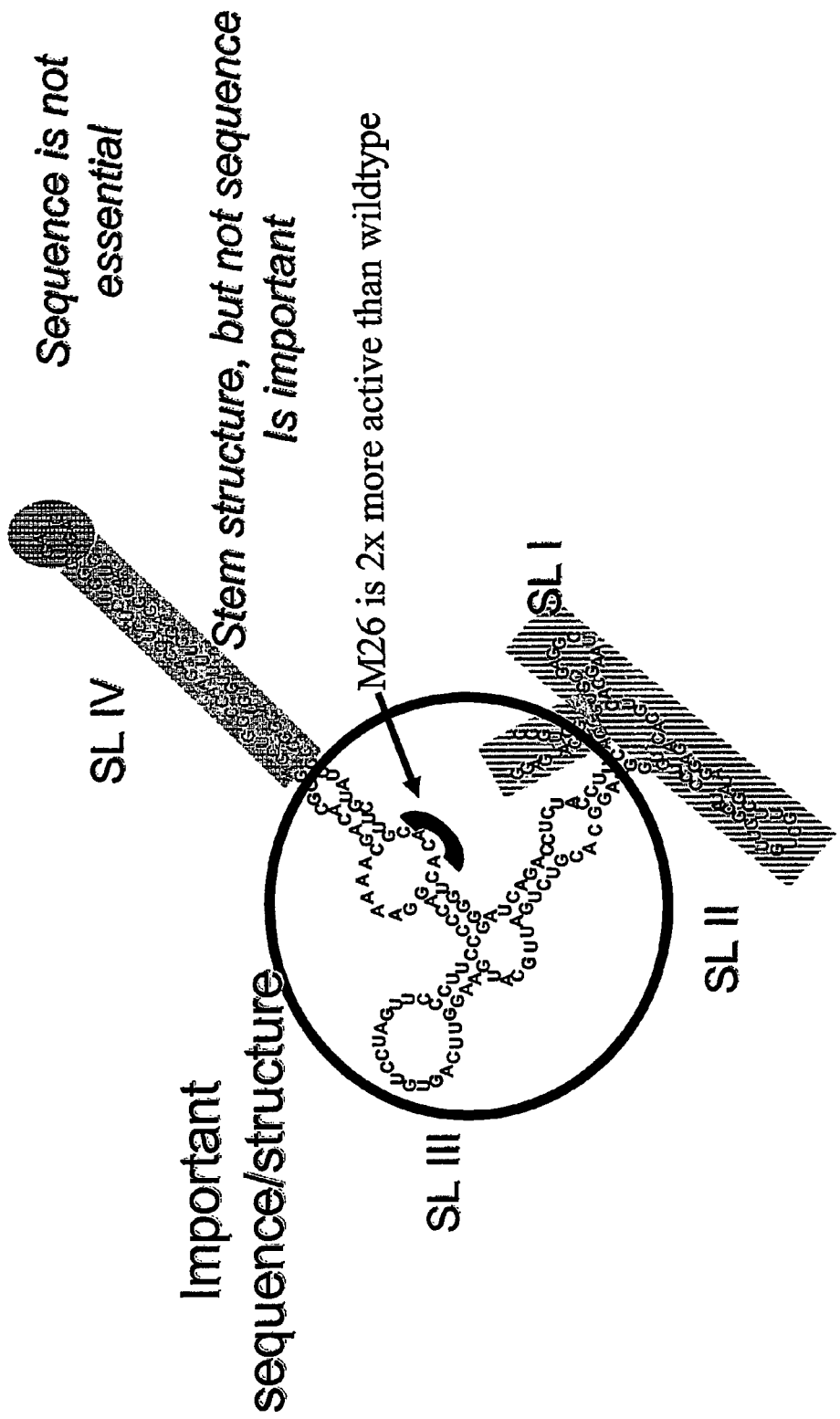
FIG. 14 provides a schematic of the structure of RTE (SEQ ID NO:5) showing important structural features.

A schematic of the complex structural arrangement of RTE is shown in FIG. 14. As in the case of CTE, several structural regions within the RTE are essential in terms of function, but not the primary sequence. These regions are not the primary interaction site for the cellular factor mediating export. Thus, substitutions may be present in these regions relative to the sequence shown in FIG. 14, so long as structure is conserved. With regard to FIG. 14, SL I and SL II are dispensable for transport function from *Xenopus* oocyte nucleus, but are important for mRNA export from mammalian cells.

Figure 15A:
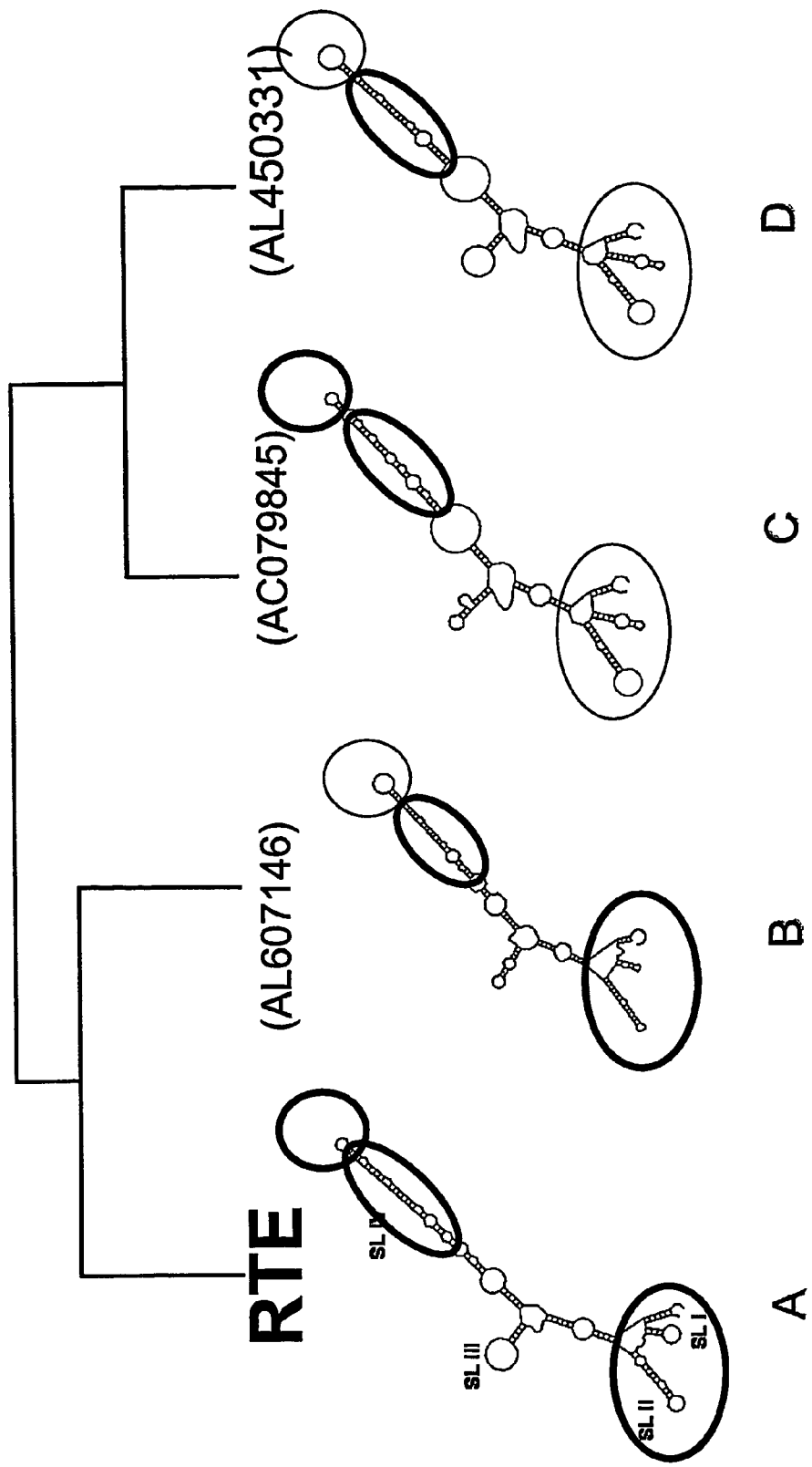
FIG. 15A shows a structural prototype of each of four major RTE families that were identified based RTE-like elements in the mouse genome. Conservation of overall structural arrangement is shown.

A search of the mouse genome identified more than 3000 RTE-like elements in that fall into 4 major families. A prototype of each family is shown in FIG. 15A (structure) and FIG. 15C (alignment). FIG. 15B shows the alignment of the consensus of each family. There is a conservation overall structure. One difference among them is stem loop IV, but experimentally, either loop functions. Thus, RTEs for use in the invention can also comprise variants in stem loop IV as well as other variants that maintain the overall structure.

RTE variants can be evaluated for function by the ability to mediate RNA transport using known assays, e.g., using an assay such as a Xenopus oocyte assay. Exemplary functional assays are provided in the examples and in WO 99/61596. RTEs for use in the invention increase expression at a level equivalent to that of wt RTE or RTEM26.

CTE Sequence

CTE sequences are known in the art. CTE sequences for use in the invention include variant CTEs that retain the ability to mediate RNA export. Exemplary CTE sequences are provided, e.g., in von Gegerfelt & Felber, *Virology* 232:291-299, 1997; and U.S. Pat. No. 5,880,276; Bray, et al., *Proc Natl Acad Sci USA* 91:1256-1260, 1994; and Tabernero, et al., *J Virol* 70:5998-6011, 1996.

In simian retrovirus type 1 (SRV-1), the core CTE spans 173 nucleotides and is sufficient for the propagation of a RRE/Rev-deficient molecular clone of HIV-1. Computer analysis and confirming mutagenesis studies suggest an RNA secondary structure consisting of an extended stem-bulge-loop. Similar structures are obtained for the simian retrovirus type 2 (SRV-2) and Mason-Pfizer monkey virus (MPMV) CTEs. SRV-1, SRV-2, and MPMV have high degrees of sequence homology in the regions panning the core CTE: 88% between SRV-1 and SRV-2 and 92% between SRV-1 and MPMV.

Variant CTEs for use in this invention typically maintain the stem loop structure, including maintaining the distance between the two loops. (See, e.g., Tabernero, et al., *J Virol* 70:5998-6011, 1996, for a schematic of the SRV-1CTE). Exemplary variants that maintain function are often in regions that are not conserved between the SRV-1, SRV-2, and MPMV sequences. For example, nucleotide composition of the hairpin is not absolutely conserved between SRV-2, MPMV, and SRV-1. Tabernero et al, supra, provide additional guidance in generating variant CTE sequences. For example, mutant 19 (Tabernero, et al., *J Virol* 70:5998-6011, 1996 on page 6005) has 12 of 173 nts that are different relative to the SRV-1 sequence, but maintains the stem structure separating the internal loops. This mutant functions like wild type CTE, while mutant 17, in which this region is deleted, is inactive. Thus, variants useful in the invention include those that have compensatory changes, but do not affect the two internal loop regions that represent the binding sites for the cellular export factor TAP/NXF1.

Exemplary assays for evaluating CTE function are provided in the examples and in reference cited herein. CTEs for use in the invention have a level of function that is equivalent to a wildtype CTE.

Positioning of the RTE and CTE Elements

The vectors of the invention comprise expression cassettes that encode transcripts having both an RTE and CTE present. The RTE and CTE may be in any order, i.e., the RTE may be present upstream of the CTE; or the CTE may be present upstream of the RTE. The spacing between the RTE and CTE is typically less than 200, 100, or 50 nucleotides. In some embodiments, the RTE and CTE are separated by 30 nucleotides or less.

The RTE and CTE combination can be present in any position, e.g. 5' to the gene to be expressed, 3' to the gene to be expressed, or within an intron, but is typically contained in the 3' untranslated region of a transcript.

Determination of Increased Expression

The ability of an RTE/CTE combination to enhance expression can be determined using any of a number of assays that are well-known in the art. Enhanced expression can be determined relative to a control that comprises only an RTE, e.g., shown in FIG. 1, or only a CTE, e.g., SEQ ID NO:4.

The level of expression of a gene can be analyzed by measuring the level of RNA transcript and/or by measuring the level of a protein encoded by the gene. RNA transcript levels can be determined using various techniques, including reverse transcription and amplification of, northern blotting, dot blotting, RNase protection, and the like. The level of a protein can be determined using convenient techniques such as western blotting or other immunoassays that employ an antibody to the protein encoded by the gene of interest. Alternatively, protein activity levels could also be used to assess gene expression.

Any gene of interest can be encoded by the expression vectors of the invention. For example, it may be desirable to use the RTE/CTE combination to enhance expression of genes that can be difficult to expression, e.g., lymphokines or cytokines. Examples of cytokines include GM-CSF, the interleukins, especially IL-1, IL-2, IL-4, IL-12, IL-10, IL-19, IL-20, interferons of the alpha, beta and gamma subtypes. Chemokines can also be delivered using expression vectors of the invention. Examples of chemokines include platelet factor 4 (PF4), platelet basic protein (PBP), interleukin-8 (IL-8), melanoma growth stimulatory activity protein (MGSA), macrophage inflammatory protein 2 (MIP-2), pre-B cell growth stimulating factor (PBSF), monocyte chemotactic proteins, macrophage inflammatory proteins, RANTES, and many others.

Other genes of interest can also be delivered for therapeutic applications. Examples of genes for therapeutic application include genes that encode immunogenic proteins for which it is desired to induce a cellular and/or humoral immune response and genes that encode cytostatic products where the expression of the product in a cell produces an arrest in the cell cycle (e.g., p21, the retinoblastoma gene product, and the like). The expression vectors of the invention can also be used to deliver growth factors or other hormones, e.g., insulin, growth hormone, nerve growth factor, vascular endothelial growth factor, and various polypeptides that have angiogenic or anti-angiogenic activity; gene products involved in apoptosis or tumor suppression; or pro-drug activating genes.

Further an RTE/CTE combination can be used to enhance transcript levels of other sequences, e.g., RNA sequences, encoded by an expression vector. These include sequences such as antisense RNA sequences or ribozymes.

Introduction of Expression Vectors into Cells

Standard transfection methods are used to introduce the expression vectors of the invention into cells. The expression vectors can be plasmid expression vectors or other commonly used expression vectors such as viral expression vectors. Gene transfer techniques include the use of calcium phosphate transfection, polybrene, protoplast fusion, electroporation, liposomes, microinjection, plasma vectors, viral vectors and any of the other well known methods for introducing heterologous nucleic acids into a host cell (see, e.g., Russell & Sambrook, supra). The vectors can be used for in vitro experiments or in vivo.

The cells are typically mammalian cells, e.g., human cells. Cells into which the vectors are introduced can be primary cells as well as cell lines. Exemplary cell types include circulating cells such as peripheral blood cells, monocytes, lymphocytes, and cells of these lineages, including CD4$^+$ T cells, and the like; muscle cells, epidermal cells, neuronal cell types, fibroblasts, hepatocytes, cardiac cells, mammary cells, prostate cells, pancreatic cells, lung cells, endocrine cells, splenocytes, and the like. Such cells may be normal or cancerous.

Non-Viral Delivery Methods

Methods of non-viral delivery of nucleic acids comprising the RTE/CTE combinations of the invention include lipofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. No. 5,049,386, U.S. Pat. No. 4,946,787; and U.S. Pat. No. 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells either in vitro or in vivo.

The preparation of lipid:nucleic acid complexes, including targeted liposomes such as immunolipid complexes, is well known to one of skill in the art (see, e.g. Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

Viral Delivery Methods

The use of RNA or DNA viral based systems for the delivery of vectors comprising the RTE/CTE combinations are known in the art. Conventional viral based systems can include lentivirus, retroviral, adenoviral, adeno-associated, herpes simplex virus, and various other viral vectors for gene transfer.

In many applications, it is desirable a vector be delivered with a high degree of specificity to a cell type, e.g., for delivery in vivo. A viral vector can be modified to have specificity for a given cell type by expressing a ligand as a fusion protein with a viral coat protein on the viruses outer surface. The ligand is chosen to have affinity for a receptor known to be present on the cell type of interest. For example, Han et al., *PNAS* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other pairs of virus expressing a ligand fusion protein and target cell expressing a receptor. For example, filamentous phage can be engineered to display antibody fragments (e.g. Fab or Fv) having specific binding affinity for virtually any chosen cellular receptor. Although the above description applies primarily to viral vectors, the same principles can be applied to nonviral vectors. Such vectors can be engineered to contain specific uptake sequences thought to favor uptake by specific target cells.

Vectors can be delivered in vivo by administration to an individual patient, typically by systemic administration (e.g., intravenous, intraperitoneal, intramuscular, subdermal, or intracranial infusion) or topical application, as described below. Alternatively, vectors can also be delivered to cells in vitro. Such methods include ex vivo methods, e.g., for introducing DNA into cells explanted from an individual patient.

Ex vivo cell transfection for diagnostics, research, or for gene therapy (e.g., via re-infusion of the transfected cells into the host organism) is well known to those of skill in the art. In some embodiments, cells are isolated from the subject organism, transfected with expression vectors comprising the RTE/CTE combination and re-infused back into the subject organism (e.g., patient). Various cell types suitable for ex vivo transfection are well known to those of skill in the art (see, e.g., Freshney et al., Culture of Animal Cells, A Manual of Basic Technique (3rd ed. 1994)) and the references cited therein for a discussion of how to isolate and culture cells from patients).

Vectors (e.g., lentiviruses, retroviruses, adenoviruses, liposomes, etc.) containing therapeutic nucleic acids can also be administered directly to an organism for transduction of cells in vivo. Alternatively, naked DNA can be administered. Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route.

The data obtained from cell culture assays and animal studies can be used to formulate a dosage range for use in humans. The dosage can vary within this range depending upon the dosage form employed and the route of administration.

When administering a viral vector, the amount of virus (number of virions) per dose will vary depending on results of different titrations used in clinical trials. The range can range, e.g., from only a few infectious units, to about $10^4$ to $10^{10}$ infectious units (i.e., virions) per dose. Protocols and means to determine safety and efficacy used for other attenuated vaccines can be adapted and used with the novel reagents provided by the invention; see, e.g., Belshe (1998) *N. Engl. J. Med.* 338:1405-1412; Gruber (1997) *Vaccine* 15:1379-1384; Tingle (1997) *Lancet* 349:1277-1281; Varis (1996) *J. Infect. Dis.* 174:S330-S334; Gruber (1996) *J. Infect. Dis.* 173:1313-1319.

The vaccine can be administered in conjunction with other treatment regimens, e.g., it can be coadministered or administered before or after any anti-viral pharmaceutical (see, e.g., Moyle (1998) *Drugs* 55:383-404) or a killed (completely inactivated) anti-HIV vaccine. The vaccine can be administered in any form of schedule regimen, e.g., in a single dose, or, using several doses (e.g., boosters) at dosages and time intervals to be determined by clinical trials.

Pharmaceutically acceptable carriers are determined in part by the particular composition being administered, as well as by the particular method used to administer the composition. Accordingly, there is a wide variety of suitable formulations of pharmaceutical compositions of the present invention, as described below (see, e.g., *Remington's Pharmaceutical Sciences*, 17th ed., 1989).

Kits

The invention also includes kits that contain the RTE/CTE combination expression vectors. Such kits can be prepared from readily available materials and reagents.

EXAMPLES

Example 1

The Presence of REM and CTE in Combination Enhances Expression

Figure 3:
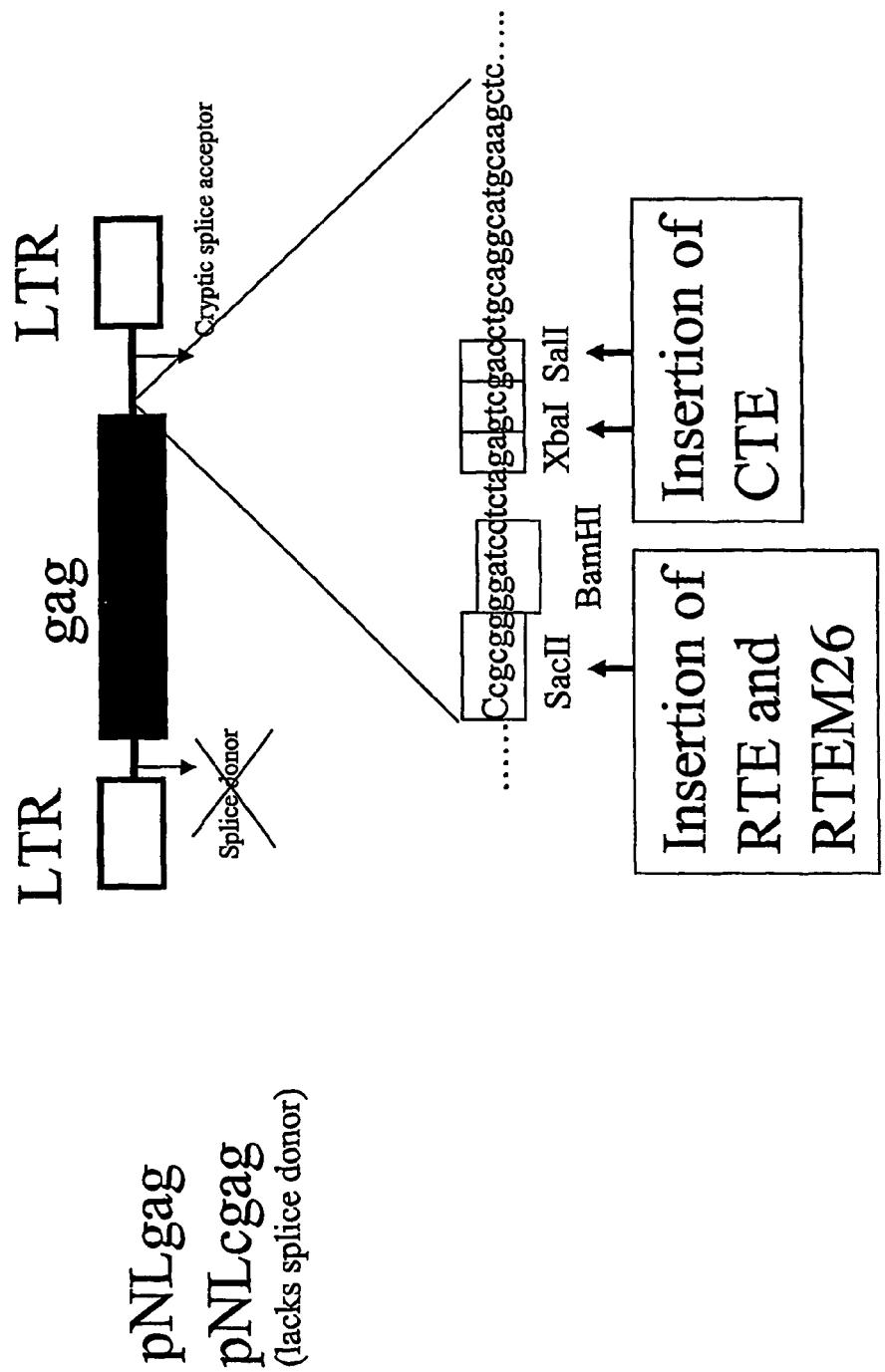
FIG. 3 shows the gag reporter plasmid and the sites where the RTE and CTE are inserted (SEQ ID NO:6).
Figure 4:
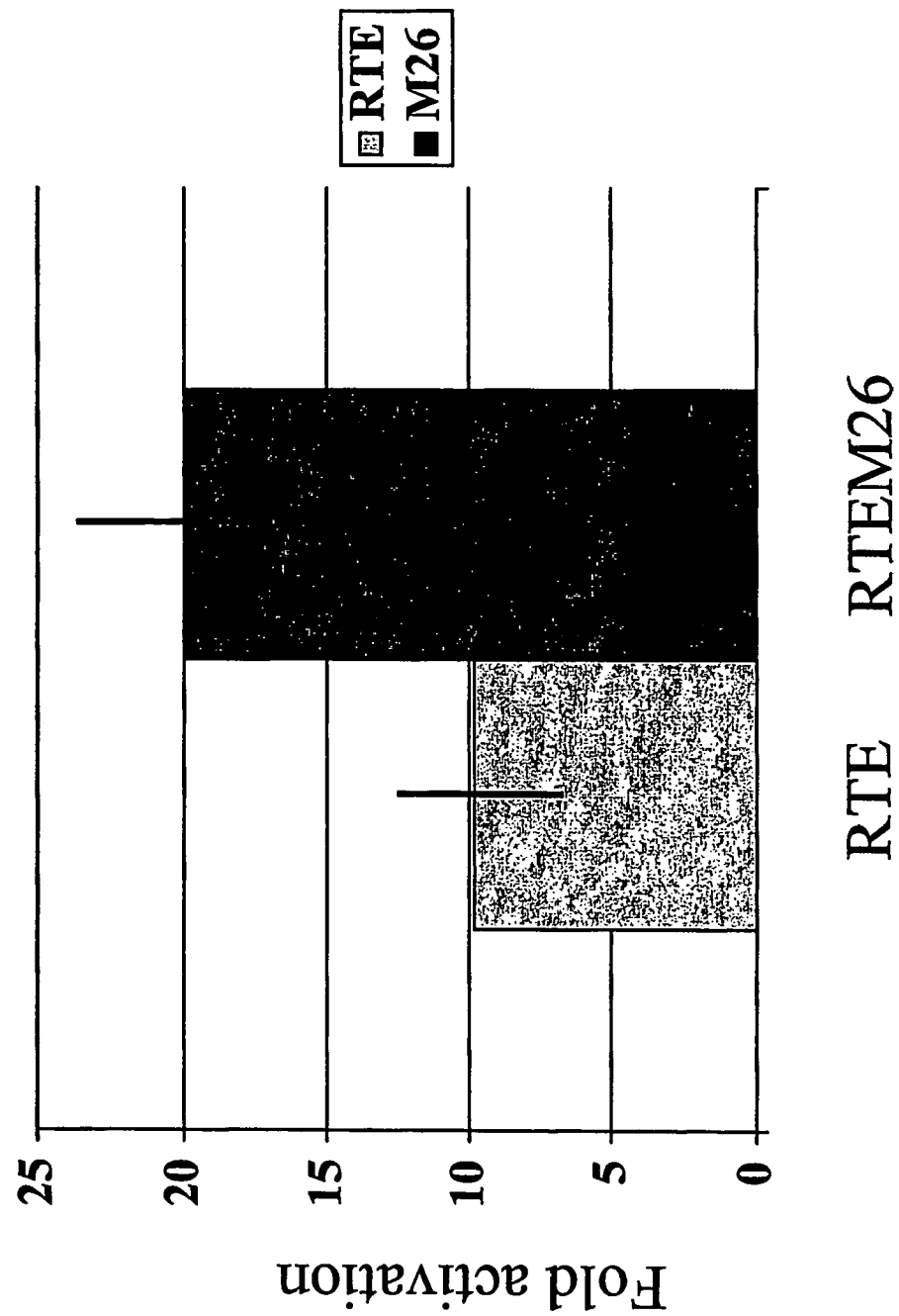
FIG. 4 provides exemplary data showing that RTEM26 increases gag expression in comparison to RTE. Values are shown with standard deviations.

Several mutant RTE elements were tested. Of these RTEM26 (FIG. 1 to 4) increased gag expression by 2-fold as compared to the wild type element (FIG. 4). The RTE element RTEM26 has 4 nucleotides changed, which does not affect the modeled structure shown in (FIG. 1).

We also tested several mutants of CTE to mediate expression of HIV-1 gag in mammalian cells. These mutants did not function better than the wild-type CTE from simian type D retrovirus-1 (SRV-1) (see, e.g., Tabernero, et al., *J Virol* 71:95-101, 1997; Tabernero, et al., *J Virol* 70:5998-6011, 1996).

Figure 6:
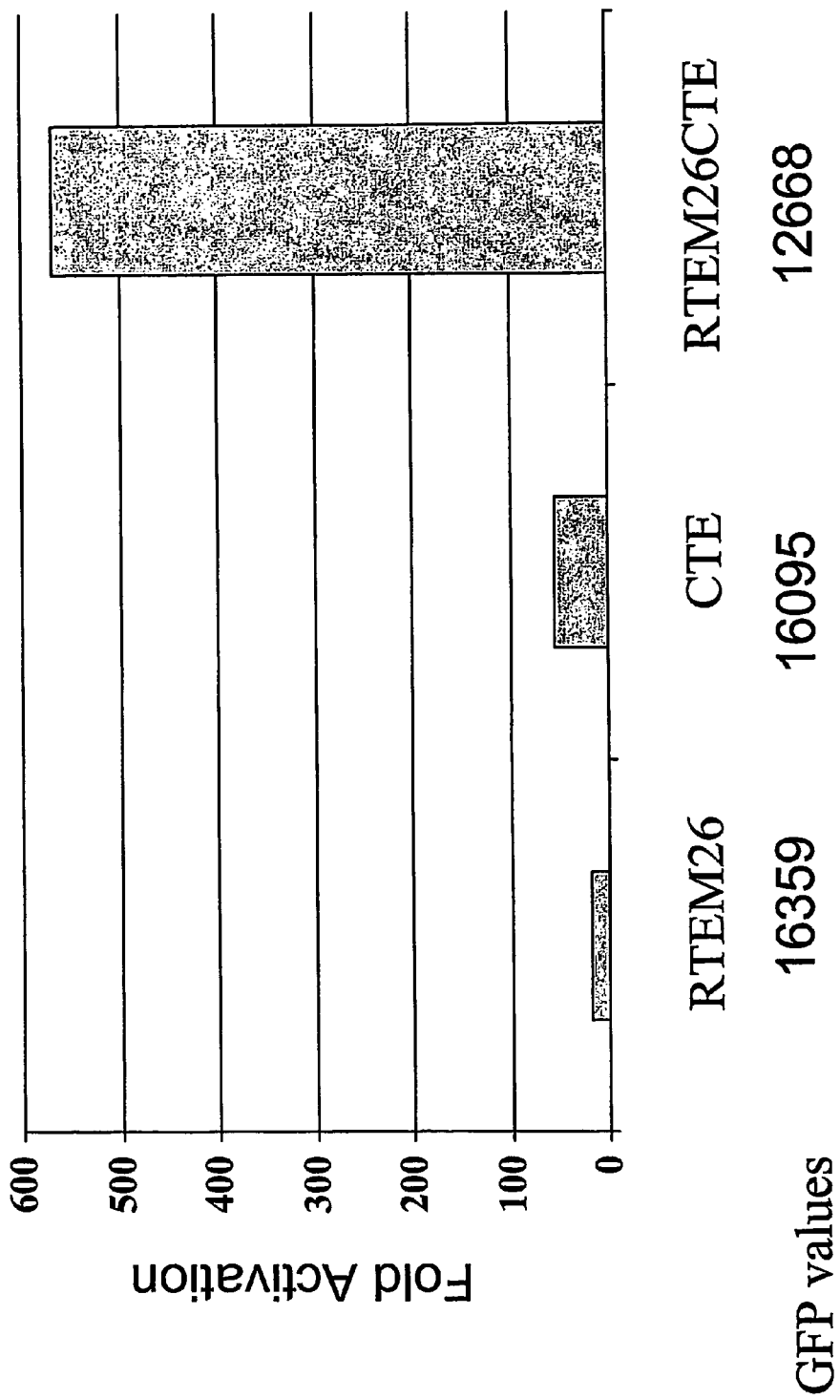
FIG. 6 provides exemplary data that shows that RTEM26CTE increases gag expression.

We found that a combination of a mutated RTE (RTEM26) positioned next to the CTE in cis (FIG. 5) has a potent effect on mRNA transport, leading to a more than 10× improved expression of unstable mRNAs, compared to either element alone. Using the HIV-1 gag as reporter mRNA, we found that RTE alone and CTE alone result in ~20× and ~50× increased expression, respectively, while the combination of these elements yielded about a ~500× fold increase in Gag expression (FIG. 6). Similar levels of green fluorescent protein (GFP) were produced from co-transfected plasmid pFRED25, used as the internal control. Therefore, the combination of RTEM26 and CTE provides a unique method to greatly activate expression of gag, which is otherwise expressed very poorly.

Figure 7:
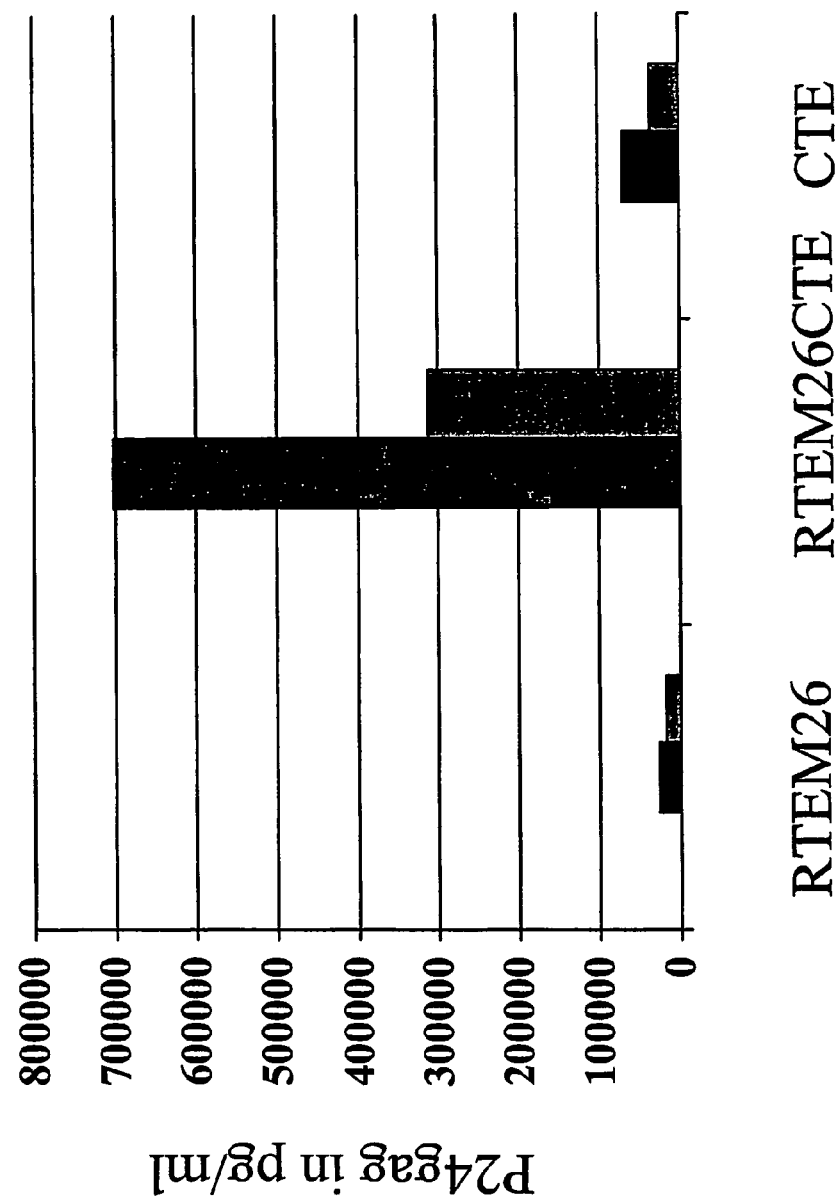
FIG. 7 provides exemplary data that shows that enhanced expression mediated by RTE-CTE combinations is independent of cell type. The dark shading represents experiments performed in HeLa HLtat cells. The lighter shading represents experiments performed in human 293 cells.

We further showed that this effect is independent of the cell type, since similar data were obtained in HeLa and 293 cells (FIG. 7).

Figure 8:
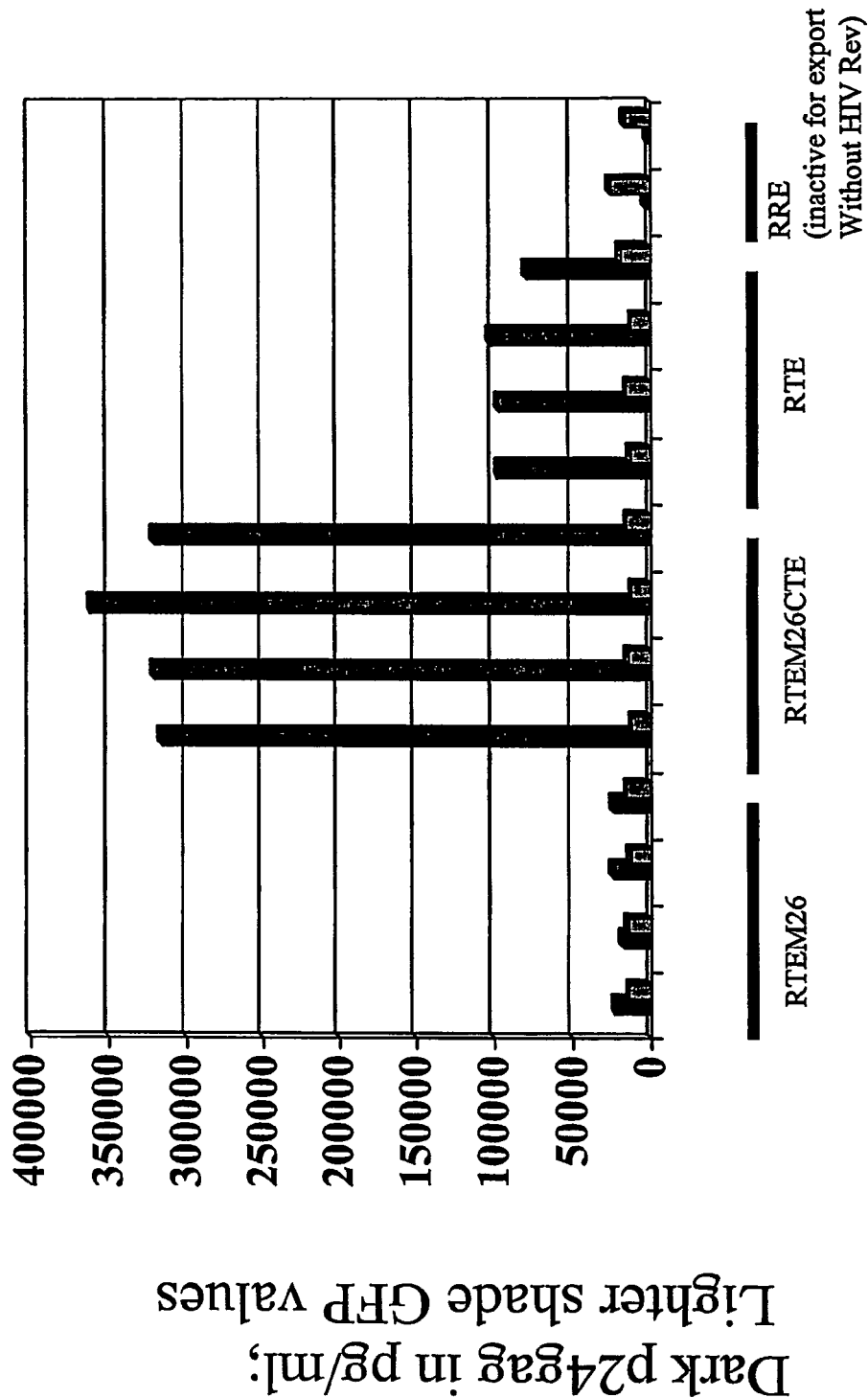
FIG. 8 provides exemplary data showing that enhanced expression mediated by RTE-CTE combinations is independent of splice sites.
Figure 9:
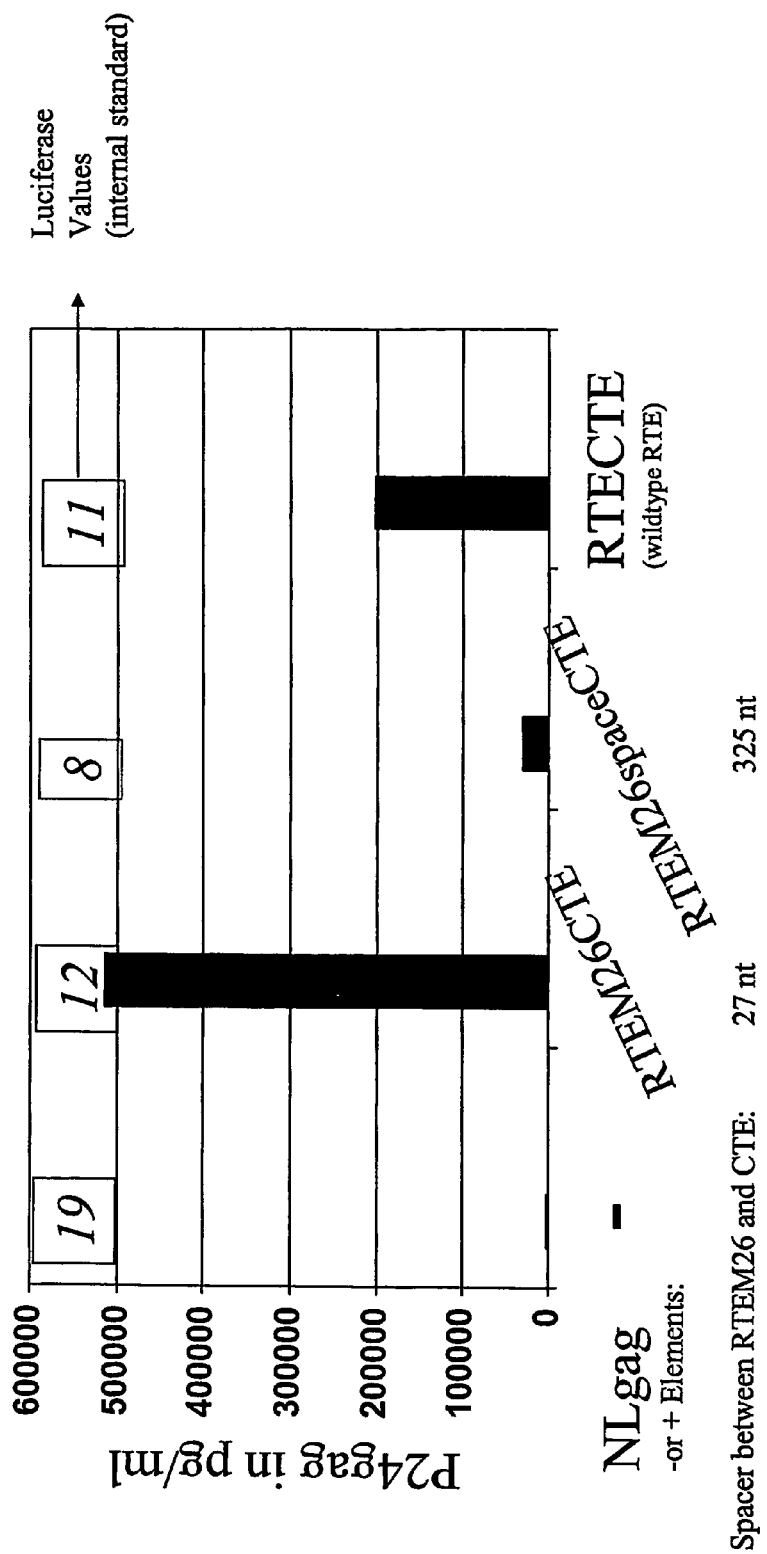
FIG. 9 shows the effects of spacing on the enhanced expression mediated by RTEM26/CTE combinations.

We also found that this effect on the gag mRNA is independent of splice sites, since we inserted RTEM26, CTE and the combination into pNLcgag, which lacks the major splice donor of HIV-1 located 5' to the gag gene (FIG. 8). We also found a potent effect on gag expression from this plasmid. The ability of RTEM26-CTE to increase expression was influenced by the spacing. When RTEM26 and CTE were separated by 325 nucleotides, synergism was not observed. When RETM26 and CTE were separated by a short distance, e.g., 27 nt, enhanced expression was pronounced. Mutations in RTEM26 also markedly transduced an increase in expression relative to wildtype RTE.

Materials and Methods

Generation of RTEM26

The wild type RTE element spanning 226 nt (previously referred to as RTE 391-616 in Nappi, et al., *J Virol* 75: 4558-69, 2001 and now numbered 1-226) was used to introduce nucleotide changes using PCR methodology. The RTE designated RTEM26 has nucleotides (#190-193) CACA changed to GCGG.

Description of NLgagRTE, NLgagRTEM26, NLgagCTE, NLgagRTEM26CTE

We used the pNLgag expressing the HIV-1 p55gag gene as reporter plasmid (Felber, et al., *Proc Natl Acad Sci USA* 86:1495-1499, 1989; Hadzopoulou-Cladaras, et al., *J Virol* 63:1265-1274, 1989; Solomin, et al., *J Virol* 64:6010-6017, 1990). In this plasmid, the gag gene is flanked by the HIV-1 LTRs which act as promoter and polyadenylation signal, respectively (FIG. 3). The RTE and RTEM26 were inserted into the SacII site located 3' to the gag gene. Subsequently, CTE was inserted into the XbaI-SalI sites located 3' to the RTEM26, generating the NLgagRTEM26CTE.

Transfection

Human HLtat, a HeLa derivative producing HIV tat (used to activate the LTR promoter) or human 293 cells were transfected with 1 μg of the NLgag plasmids (for 293 cells a tat expression plasmid pBstat was cotransfected). We routinely analyzed 2-3 independent clones in duplicate. We contransfect pFRED25 (0.8 μg) as internal control. All transfections were performed using FUGENE-6. Two days later, the cells were harvested in Tris-Triton lysis buffer and the cell extracts were analyzed for Gag expression using a commercial (Zeptometrix) HIV gag antigen capture assay and for GFP production.

Example 2

Enhanced Expression of HIV-1 env

Figure 10A:
FIGS. 10A and 10B present exemplary data that show the effect of RTEM26-CTE on HIV-1 envelope expression.
Figure 10B:
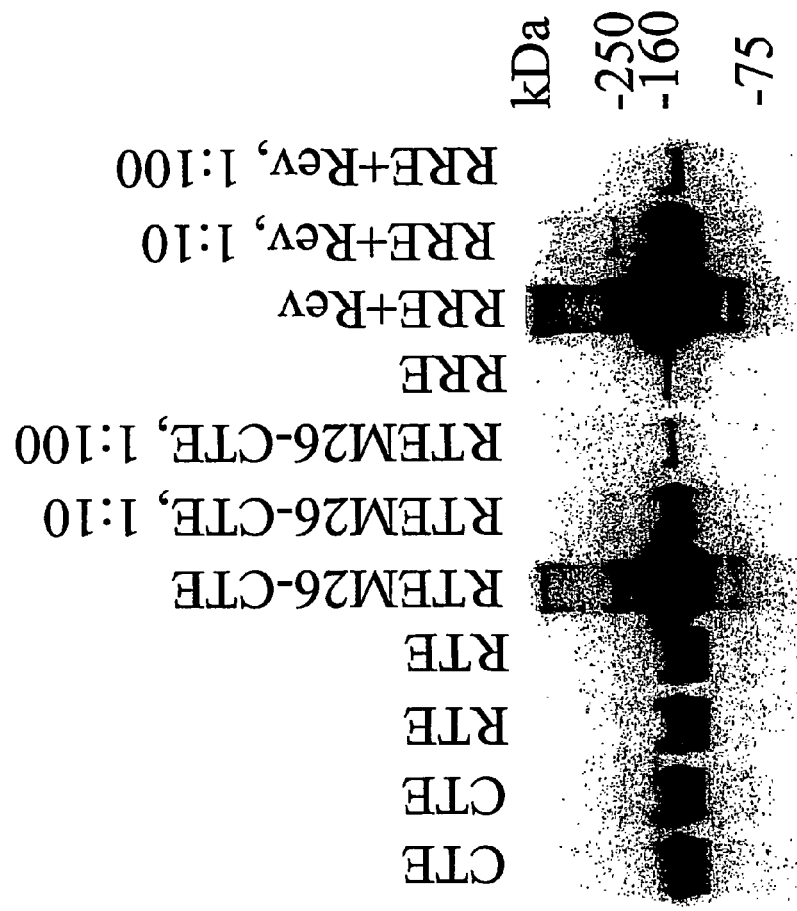

An expression vector was constructed to express the HIV env protein (FIGS. 10A and 10B.) A schematic of the plasmid is shown in FIG. 10A. To evaluate expression, 293 cells were transfected with the plasmid and 2 days later, cell extracts were prepared. The extracts were analyzed for HIV env expression by Western blot using anti-HIV env serum. The levels of the env produced from the cDNA containing the RRE was very low in the absence of Rev, while the presence of Rev led to an notable increased (undiluted, 1:10, and 1:100 dilute samples are shown in FIG. 10B). Both RTE and CTE mediated an increase in env production, but the level were about 10% of those obtained in the presence of Rev. The presence of RTEN26CTE led to levels comparable to those obtained in the presence of Rev (undiluted, 1:10, and 1:100 dilutions).

Example 3

RTEM26CTE Mediate Enhanced Expression from the Molecular Clone SIV R-R-Δnef

Figure 11A:
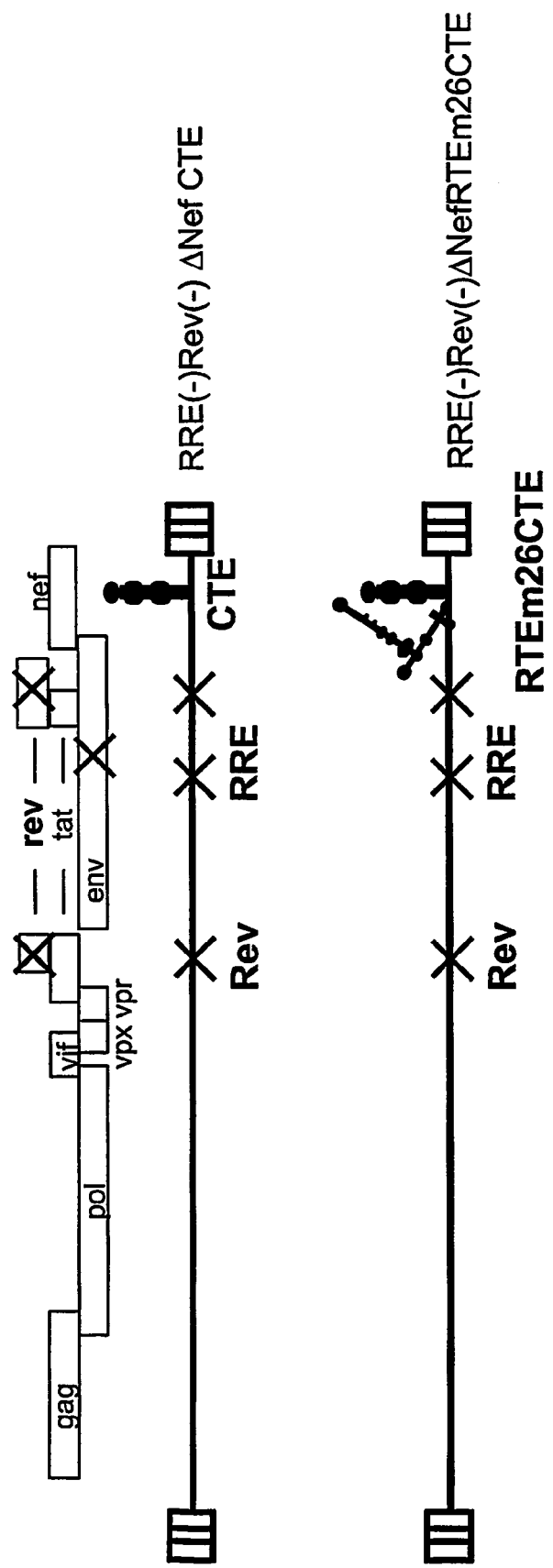
FIGS. 11A and 11B provides exemplary data showing that RTEM26CTE synergistically increases expression from molecular clone SIV R-R-Δnef.
Figure 11B:
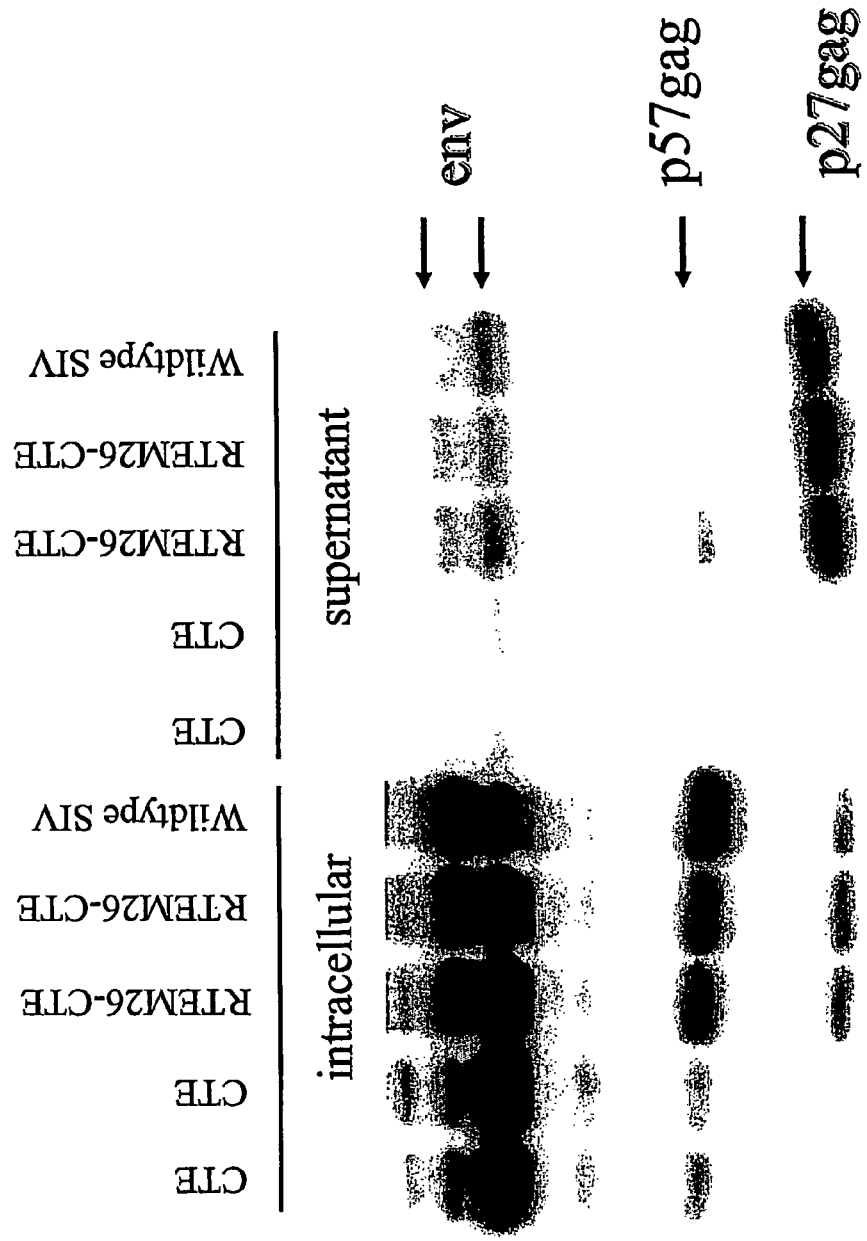

FIG. 11A shows a schematic of the Rev(−)RRE(−)Δnef CTE(+)SIVmac239 clones into which RTEM26 was cloned. Expression of the plasmid was evaluated in 293 cells. Western blot analysis shows a dramatic increase in expression of the RTEM26cTE-containing cells compared to cells transfected with a plasmid containing CTE only. The levels are similar to those obtained from the wild type virus. This shows that RTEM26CTE is a powerful mediator of expression of a complex array of mRNAs produced from the full length mRNA.

The RTE/CTE combination was also tested in plasmids that were previously optimized for expression. The presence of RTEM26CTE in such vectors elevated expression about 2-3-fold in human 293 cells (data not shown). In some embodiments, an RTE/CTE combination can be used in previously optimized vectors to introduce the vectors into primary cells for increased expression.

Example 4

RTE/CTE Configuration

Figure 12:
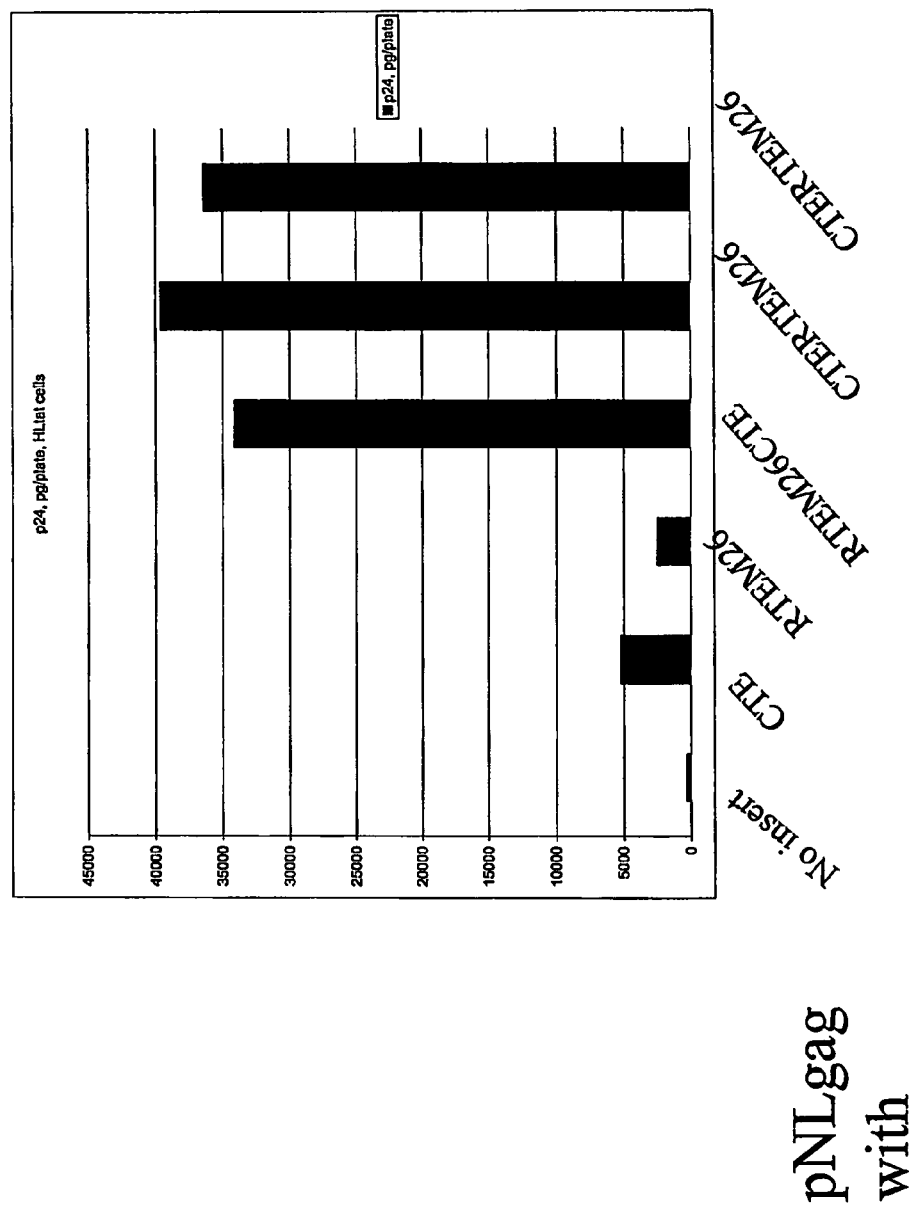

The configuration of the RTEM26-CTE combination was also examined. FIG. 12 provides exemplary data showing that the position of the individual elements within the RTEM26CTE combination is interchangeable. The RTEM26 in RTEM26CTE is 5' to CTE, while in CTERTEM26 it is 3' to the CTE.

Figure 13:
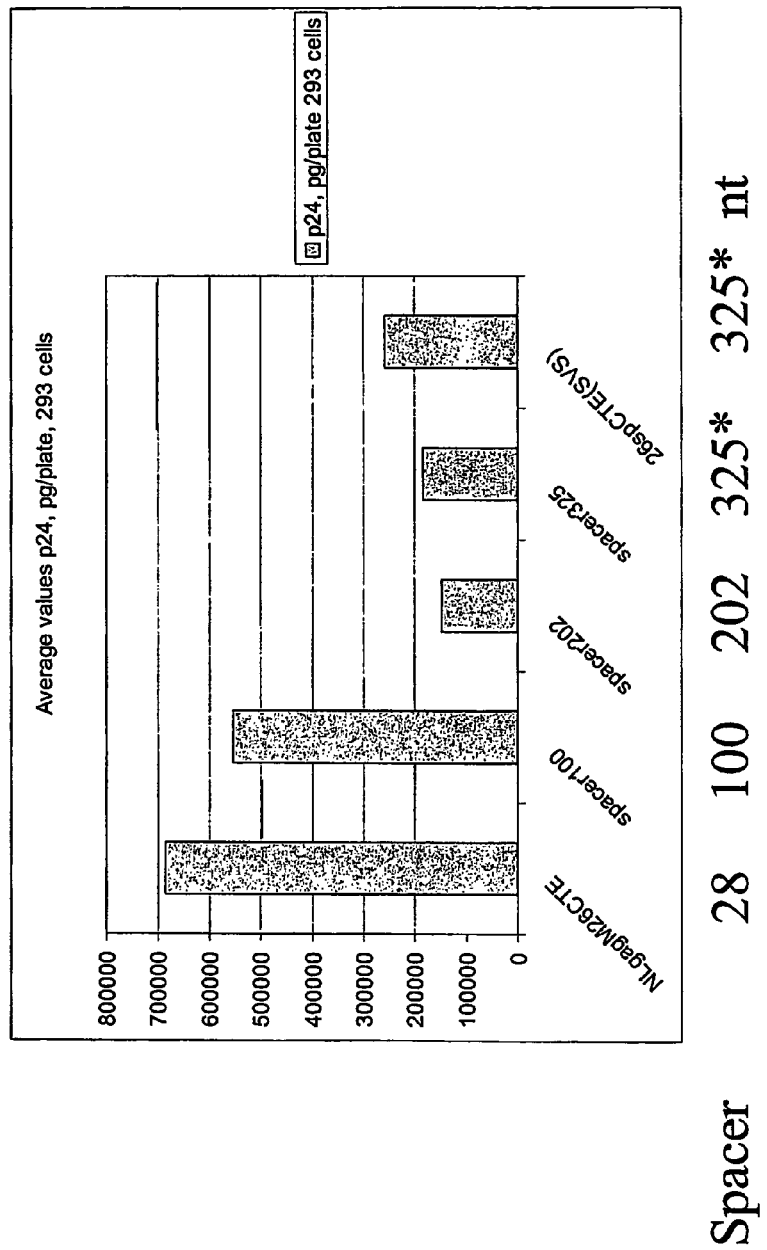
FIG. 13 provides exemplary data showing that the length of the spacer between the RTE and CTE elements is important for optimal function.

FIG. 13 shows that the length of the spacer between the element between 28 nt (original RTEM26CTE) is important for optimal function. Increasing the distance to 202 or 325 nt reduces the effect of RTEM26CTE. Distances between the elements of 100 nt and 28 nt yield similar results.

The above examples are provided by way of illustration only and not by way of limitation. Those of skill in the art will readily recognize a variety of noncritical parameters that could be changed or modified to yield essentially similar results.

All publications, patent applications, accession numbers, and other references cited in this specification are herein incorporated by reference as if each individual publication, patent application, accession number or other reference was specifically and individually indicated to be incorporated by reference.

```
TABLE OF SEQUENCES
SEQ ID NO: 1
RTE wildtype sequence
CCGTGGGGTGCGAGGCTAAGCACTGCACAGAGGATAGCTTGCTGTTGGCATCCT

GTGGAAGGCACGTCTGATTGCATGAAGGTTCAGTGTCCTAGTTCCCTTCCCCCAG

GAAAAACGACACGGGAGCTGGCCAAGACCTCTCTGGGTGATGAGCCTAAGGGAT

GGTTTTGTGTAGGGCCCCTATGCTTGCACACTGGGGATCAGACCTCTACCTTCAC

CCATGAGG

SEQ ID NO: 2
RTEM26 nucleotide sequence of mutant RTEM26; the lower case
letters indicate the four differences with RTEwt
CCGTGGGGTGCGAGGCTAAGCACTGCACAGAGGATAGCTTGCTGTTGGCATCCT

GTGGAAGGCACGTCTGATTGCATGAAGGTTCAGTGTCCTAGTTCCCTTCCCCCAG

GAAAAACGACACGGGAGCTGGCCAAGACCTCTCTGGGTGATGAGCCTAAGGGAT

GGTTTTGTGTAGGGCCCCTATGCTTGgcggCTGGGGATCAGACCTCTACCTTCACCC

ATGAGG

SEQ ID NO: 3
RTEM26CTE nucleotide sequence of a preferred combination RTE-CTE
element; lower case letters indicate the differences with the
RTEwt and the spacer region.
CCGTGGGGTGCGAGGCTAAGCACTGCACAGAGGATAGCTTGCTGTTGGCATCCT

GTGGAAGGCACGTCTGATTGCATGAAGGTTCAGTGTCCTAGTTCCCTTCCCCCAG

GAAAAACGACACGGGAGCTGGCCAAGACCTCTCTGGGTGATGAGCCTAAGGGAT
```

GGTTTTGTGTAGGGCCCCTATGCTTGgcggCTGGGGATCAGACCTCTACCTTCACCC

ATGAGGtatcgataccgcgggatcctctagagtAGACCACCTCCCCTGCGAGCTAAGCTGGACA

GCCAATGACGGGTAAGAGAGTGACATTTTTCACTAACCTAAGACAGGAGGGCCG

TCAGAGCTACTGCCTAATCCAAAGACGGGTAAAAGTGATAAAAATGTATCACTC

CAACCTAAGACAGGCGCAGCTTCCGAGGGATTTG

SEQ ID NO: 4
Exemplary CTE sequence. This CTE is from simian virus type I
(SRV-1 (Tabernero et al., J. Virol. 70: 5998-6011, 1996).
AGACCACCTCCCCTGCGAGCTAAGCTGGACAGCCAATGACGGGTAAGAGAGTGA

CATTTTTCACTAACCTAAGACAGGAGGGCCGTCAGAGCTACTGCCTAATCCAAAG

ACGGGTAAAAGTGATAAAAATGTATCACTCCAACCTAAGACAGGCGCAGCTTCC

GAGGGATTTG

---

What is claimed is:

1. An expression vector comprising an expression cassette encoding a transcript that comprises a RTE and a CTE where,
  a) the RTE has four stem-loops and i) has at least 85% identity to SEQ ID NO:1 and ii) comprises a mutation at each of positions 190, 191, 192, and 193 of SEQ ID NO:1; and
  b) the CTE has at least 85% identity to SEQ ID NO:4; wherein the presence of the RTE and CTE enhances expression of the transcript.

2. The vector of claim 1, wherein the CTE comprises the sequence set forth in SEQ ID NO:4.

3. The vector of claim 1, wherein the RTE comprises the sequence set forth in SEQ ID NO:2.

4. The vector of claim 1, wherein the RTE and the CTE are positioned in the 3' untranslated region of a transcript encoded by the expression cassette.

5. The vector of claim 1, wherein the RTE and the CTE are separated by 200 nucleotides or less.

6. The vector of claim 1, wherein the RTE and the CTE are separated by 30 nucleotides or less.

7. The vector of claim 6, wherein the RTE and the CTE are comprised by the sequence set forth in SEQ ID NO:3.

8. The vector of claim 1, wherein the expression cassette comprises a sequence encoding a viral gene product.

9. The vector of claim 8, wherein the sequence encoding a viral gene product is a retrovirus gene.

10. The vector of claim 9, wherein the retrovirus gene is HIV-1 gag.

11. The vector of claim 9, wherein the retrovirus gene is HIV-1 env.

12. The vector of claim 1, wherein the vector is a lentiviral vector.

13. An expression vector comprising an expression cassette encoding a transcript that comprises an RTE that comprises the sequence set forth in SEQ ID NO:2.

14. A host cell comprising an expression vector of claim 1 or claim 13.

15. A method of enhancing expression of a transcript encoded by an expression vector, the method comprising introducing into a eukaryotic cell, a vector comprising an expression cassette encoding a transcript that comprises a RTE and a CTE, where:
  a) the RTE has four stem loops and i) has at least 85% identity to SEQ ID NO:1; and ii) comprises a mutation at each of positions 190, 191, 192, and 193 of SEQ ID NO:1; and
  b) the CTE has at least 85% identity to SEQ ID NO:4; wherein the presence of the RTE and CTE increases expression of the transcript.

16. The method of claim 15, wherein the CTE comprises the sequence set forth in SEQ ID NO:4.

17. The method of claim 15, wherein the RTE comprises the sequence set forth in SEQ ID NO:2.

18. The method of claim 15, wherein the RTE and the CTE are positioned in the 3' untranslated region of a transcript encoded by the expression cassette.

19. The method of claim 15, wherein the RTE and the CTE are separated by 200 nucleotides or less.

20. The method of claim 15, wherein the RTE and the CTE are separated by 30 nucleotides or less.

21. The method of claim 15, wherein the expression cassette comprises a sequence encoding a viral gene product.

22. The method of claim 21, wherein the sequence encoding a viral gene product is a retrovirus gene.

23. The method of claim 22, wherein the retrovirus gene is HIV-1 gag.

24. The method of claim 22, wherein the retrovirus gene is HIV-1 env.

25. The method of claim 15, wherein the vector is a lentiviral vector.

26. The vector of claim 1, wherein the RTE comprises the sequence set forth in SEQ ID NO:2 and the CTE comprises the sequence set forth in SEQ ID NO:4, wherein the RTE and CTE are separated by 200 nucleotide or less.

27. An expression vector comprising an expression cassette encoding a transcript that comprises a RTE and a CTE where,
  a) the RTE has four stem loops and i) has at least 85% identity to SEQ ID NO:1 and ii) comprises a mutation at each of positions 190, 191, 192, and 193 of SEQ ID NO:1; and
  b) the CTE has at least 85% identity to SEQ ID NO:4.

28. The vector of claim 27, wherein the RTE has at least 90% identity to SEQ ID NO:1 and comprises a mutation at each of positions 190, 191, 192, and 193 of SEQ ID NO:1; and the CTE has at least 90% identity to SEQ ID NO:4.

29. An expression vector comprising an expression cassette encoding a transcript that comprises a RTE and a CTE where a) the RTE has four stem loops and i) has at least 95% identity to SEQ ID NO:1 and ii) comprises a mutation at each of positions 190, 191, 192, and 193 of SEQ ID NO:1; and b) the CTE has at least 95% identity to SEQ ID NO:4; wherein the presence of the RTE and CTE enhances expression of the transcript.

* * * * *

SEQUENCE LISTING

<160> NUMBER OF SEQ ID NOS: 13

<210> SEQ ID NO 1
<211> LENGTH: 226
<212> TYPE: DNA
<213> ORGANISM: Mus musculus
<220> FEATURE:
<223> OTHER INFORMATION: wildtype RNA transport element (RTE), RTE-like
      element family prototype
<220> FEATURE:
<221> NAME/KEY: stem_loop
<222> LOCATION: (8)..(24)
<223> OTHER INFORMATION: stem loop I (SL I)
<220> FEATURE:
<221> NAME/KEY: stem_loop
<222> LOCATION: (28)..(58)
<223> OTHER INFORMATION: stem loop II (SL II)
<220> FEATURE:
<221> NAME/KEY: stem_loop
<222> LOCATION: (78)..(104)
<223> OTHER INFORMATION: stem loop III (SL III)
<220> FEATURE:
<221> NAME/KEY: stem_loop
<222> LOCATION: (140)..(156)
<223> OTHER INFORMATION: stem loop IV (SL IV)

<400> SEQUENCE: 1
ccgtggggtg cgaggctaag cactgcacag aggatagctt gctgttggca tcctgtggaa      60
ggcacgtctg attgcatgaa ggttcagtgt cctagttccc ttcccccagg aaaaacgaca     120
cgggagctgg ccaagacctc tctgggtgat gagcctaagg gatggttttg tgtagggccc     180
ctatgcttgc acactgggga tcagacctct accttcaccc atgagg                    226

<210> SEQ ID NO 2
<211> LENGTH: 226
<212> TYPE: DNA
<213> ORGANISM: Artificial Sequence
<220> FEATURE:
<223> OTHER INFORMATION: Description of Artificial Sequence:mutant RNA
      transport element (RTE) RTEM26

<400> SEQUENCE: 2
ccgtggggtg cgaggctaag cactgcacag aggatagctt gctgttggca tcctgtggaa      60
ggcacgtctg attgcatgaa ggttcagtgt cctagttccc ttcccccagg aaaaacgaca     120
cgggagctgg ccaagacctc tctgggtgat gagcctaagg gatggttttg tgtagggccc     180

```
ctatgcttgg cggctgggga tcagacctct accttcaccc atgagg          226
```

<210> SEQ ID NO 3
<211> LENGTH: 427
<212> TYPE: DNA
<213> ORGANISM: Artificial Sequence
<220> FEATURE:
<223> OTHER INFORMATION: Description of Artificial Sequence:RTEM26CTE
      RNA transport element (RTE)-constitutive transport
      element (CTE) combination element

<400> SEQUENCE: 3

```
ccgtggggtg cgaggctaag cactgcacag aggatagctt gctgttggca tcctgtggaa    60
ggcacgtctg attgcatgaa ggttcagtgt cctagttccc ttcccccagg aaaaacgaca   120
cgggagctgg ccaagacctc tctgggtgat gagcctaagg gatggttttg tgtagggccc   180
ctatgcttgg cggctgggga tcagacctct accttcaccc atgaggtatc gataccgcgg   240
ggatcctcta gagtagacca cctcccctgc gagctaagct ggacagccaa tgacgggtaa   300
gagagtgaca ttttcacta  acctaagaca ggagggccgt cagagctact gcctaatcca   360
aagacgggta aaagtgataa aaatgtatca ctccaaccta agacaggcgc agcttccgag   420
ggatttg                                                              427
```

<210> SEQ ID NO 4
<211> LENGTH: 173
<212> TYPE: DNA
<213> ORGANISM: Simian retrovirus SRV-1
<220> FEATURE:
<223> OTHER INFORMATION: exemplary constitutive transport element (CTE)
      sequence

<400> SEQUENCE: 4

```
agaccacctc ccctgcgagc taagctggac agccaatgac gggtaagaga gtgacatttt    60
tcactaacct aagacaggag ggccgtcaga gctactgcct aatccaaaga cgggtaaaag   120
tgataaaaat gtatcactcc aacctaagac aggcgcagct tccgagggat ttg          173
```

<210> SEQ ID NO 5
<211> LENGTH: 226
<212> TYPE: RNA
<213> ORGANISM: Artificial Sequence
<220> FEATURE:
<223> OTHER INFORMATION: Description of Artificial Sequence:mutant RNA
      transport element (RTE) RTEM26
<220> FEATURE:
<221> NAME/KEY: stem_loop
<222> LOCATION: (8)..(24)
<223> OTHER INFORMATION: stem loop I (SL I)
<220> FEATURE:
<221> NAME/KEY: stem_loop
<222> LOCATION: (28)..(58)
<223> OTHER INFORMATION: stem loop II (SL II)
<220> FEATURE:
<221> NAME/KEY: stem_loop
<222> LOCATION: (78)..(104)
<223> OTHER INFORMATION: stem loop III (SL III)
<220> FEATURE:
<221> NAME/KEY: stem_loop
<222> LOCATION: (140)..(156)
<223> OTHER INFORMATION: stem loop IV (SL IV)

<400> SEQUENCE: 5

```
ccguggggug cgaggcuaag cacugcacag aggauagcuu gcuguuggca uccuguggaa    60
ggcacgucug auugcaugaa gguucagugu ccuaguuccc uucccccagg aaaaacgaca   120
cgggagcugg ccaagaccuc ucuggguugau gagccuaagg gaugguuuug uguagggccc  180
```
cuaugcuugc acacuggggga ucagaccucu accuucaccc augagg            226

<210> SEQ ID NO 6
<211> LENGTH: 42
<212> TYPE: DNA
<213> ORGANISM: Artificial Sequence
<220> FEATURE:
<223> OTHER INFORMATION: Description of Artificial Sequence:site of RTE
      and CTE insert and spacer region in reporter plasmid

<400> SEQUENCE: 6 ccgcgggat cctctagagt cgacctgcag gcatgcaagc tc                  42

<210> SEQ ID NO 7
<211> LENGTH: 229
<212> TYPE: DNA
<213> ORGANISM: Artificial Sequence
<220> FEATURE:
<223> OTHER INFORMATION: Description of Artificial Sequence:mouse RTE
      family consensus A
<220> FEATURE:
<221> NAME/KEY: stem_loop
<222> LOCATION: (8)..(24)
<223> OTHER INFORMATION: stem loop I (SL I)
<220> FEATURE:
<221> NAME/KEY: stem_loop
<222> LOCATION: (28)..(59)
<223> OTHER INFORMATION: stem loop II (SL II)
<220> FEATURE:
<221> NAME/KEY: stem_loop
<222> LOCATION: (79)..(104)
<223> OTHER INFORMATION: stem loop III (SL III)
<220> FEATURE:
<221> NAME/KEY: stem_loop
<222> LOCATION: (143)..(159)
<223> OTHER INFORMATION: stem loop IV (SL IV)

<400> SEQUENCE: 7
ccgtggggtg cgaggctaag cactgcacag aggatagctt gactgttggc atcctgtgga    60
aggcaygtct gattgcatga aggttcagtg tcctagttcc cttcccccag gaaaaaaacg   120
acacgggagc tggccaagac ctctctgggt gatgagccta agggatggtt ttgtgtaggg   180
cccctatgct tgcacactgg ggatcagacc tctaccttca cccatgagg              229

<210> SEQ ID NO 8
<211> LENGTH: 239
<212> TYPE: DNA
<213> ORGANISM: Artificial Sequence
<220> FEATURE:
<223> OTHER INFORMATION: Description of Artificial Sequence:mouse RTE
      family consensus B
<220> FEATURE:
<221> NAME/KEY: stem_loop
<222> LOCATION: (8)..(24)
<223> OTHER INFORMATION: stem loop I (SL I)
<220> FEATURE:
<221> NAME/KEY: stem_loop
<222> LOCATION: (28)..(61)
<223> OTHER INFORMATION: stem loop II (SL II)
<220> FEATURE:
<221> NAME/KEY: stem_loop
<222> LOCATION: (82)..(107)
<223> OTHER INFORMATION: stem loop III (SL III)
<220> FEATURE:
<221> NAME/KEY: stem_loop
<222> LOCATION: (146)..(169)
<223> OTHER INFORMATION: stem loop IV (SL IV)

<400> SEQUENCE: 8
ckgagggttg taaggctaag cactgcacag aggttagtct ggagctgttt gacartctct    60

```
gggaggcayg tctgattgca tgaaggttga gtgtcctagt gtccttcccc caggaaaaaa      120
acggcacggg agcaggtcag ggttrctctg ggtaaaaayc tgtgagccta agagtcaatc      180
ctgtacatgg cccctatywt tgcacactgg ggatcagacc tctaccttca cccatggag      239
```

```
<210> SEQ ID NO 9
<211> LENGTH: 236
<212> TYPE: DNA
<213> ORGANISM: Artificial Sequence
<220> FEATURE:
<223> OTHER INFORMATION: Description of Artificial Sequence:mouse RTE
      family consensus C
<220> FEATURE:
<221> NAME/KEY: stem_loop
<222> LOCATION: (8)..(24)
<223> OTHER INFORMATION: stem loop I (SL I)
<220> FEATURE:
<221> NAME/KEY: stem_loop
<222> LOCATION: (28)..(64)
<223> OTHER INFORMATION: stem loop II (SL II)
<220> FEATURE:
<221> NAME/KEY: stem_loop
<222> LOCATION: (85)..(110)
<223> OTHER INFORMATION: stem loop III (SL III)
<220> FEATURE:
<221> NAME/KEY: stem_loop
<222> LOCATION: (149)..(165)
<223> OTHER INFORMATION: stem loop IV (SL IV)

<400> SEQUENCE: 9
```

```
gagagagttg cacggctaag cactgcagta gaagggctct gcggctawaa tgagcctatt      60
ctagggagac aygtcatctt tcaagaaggt tgagtgtcca agtgtccttc tccccagaga     120
aaaacgacac gggaccagac caggaccct ctgggtgatg agcctgggag gaggttatgt     180
gtacggctcc tattacctgc acactgggga tttgacctct atctccactc tcatta        236
```

```
<210> SEQ ID NO 10
<211> LENGTH: 243
<212> TYPE: DNA
<213> ORGANISM: Artificial Sequence
<220> FEATURE:
<223> OTHER INFORMATION: Description of Artificial Sequence:mouse RTE
      family consensus D
<220> FEATURE:
<221> NAME/KEY: stem_loop
<222> LOCATION: (8)..(24)
<223> OTHER INFORMATION: stem loop I (SL I)
<220> FEATURE:
<221> NAME/KEY: stem_loop
<222> LOCATION: (28)..(64)
<223> OTHER INFORMATION: stem loop II (SL II)
<220> FEATURE:
<221> NAME/KEY: stem_loop
<222> LOCATION: (85)..(110)
<223> OTHER INFORMATION: stem loop III (SL III)
<220> FEATURE:
<221> NAME/KEY: stem_loop
<222> LOCATION: (149)..(172)
<223> OTHER INFORMATION: stem loop IV (SL IV)

<400> SEQUENCE: 10
```

```
gagagagttg caaggctaag cactgcaatg gaaaggctct gcggctatat tgagcctatt      60
ctagggagac aygtcatctt tcatgaaggt tcagtgtcct agttcccttc tccccagagc     120
aaaacgacac gggagcaggt cagggttgct ctgggtaaaa gcctgtgagc ctaagagcta     180
atcctgtaca tggctcctat tacctacaca ctggggattt gacctctatc tccactctca     240
tta                                                                   243
```

```
<210> SEQ ID NO 11
```

```
<211> LENGTH: 235
<212> TYPE: DNA
<213> ORGANISM: Mus musculus
<220> FEATURE:
<223> OTHER INFORMATION: RNA transport element (RTE) prototype family
      member GenBank Accession No. AL607146
<220> FEATURE:
<221> NAME/KEY: stem_loop
<222> LOCATION: (8)..(24)
<223> OTHER INFORMATION: stem loop I (SL I)
<220> FEATURE:
<221> NAME/KEY: stem_loop
<222> LOCATION: (28)..(59)
<223> OTHER INFORMATION: stem loop II (SL II)
<220> FEATURE:
<221> NAME/KEY: stem_loop
<222> LOCATION: (79)..(105)
<223> OTHER INFORMATION: stem loop III (SL III)
<220> FEATURE:
<221> NAME/KEY: stem_loop
<222> LOCATION: (142)..(165)
<223> OTHER INFORMATION: stem loop IV (SL IV)

<400> SEQUENCE: 11
ccgtggattg ttgggctaag caccgcatag gagtcgctca gaggtttggg cactcctaga    60
agacaagtcg atttgcatga gggttgagtg tccaagtgtc cctcccctag gaaaaaacgg   120
cacgggagca ggtcagggtt gctctgggta aaagcctgtg agcctaagag ctaatcctgt   180
acatggcccc tatttctgca cactagggat tcgacctcta tcttcatcca ttaaa        235

<210> SEQ ID NO 12
<211> LENGTH: 234
<212> TYPE: DNA
<213> ORGANISM: Mus musculus
<220> FEATURE:
<223> OTHER INFORMATION: RNA transport element (RTE) prototype family
      member GenBank Accession No. AC079845
<220> FEATURE:
<221> NAME/KEY: stem_loop
<222> LOCATION: (8)..(24)
<223> OTHER INFORMATION: stem loop I (SL I)
<220> FEATURE:
<221> NAME/KEY: stem_loop
<222> LOCATION: (28)..(66)
<223> OTHER INFORMATION: stem loop II (SL II)
<220> FEATURE:
<221> NAME/KEY: stem_loop
<222> LOCATION: (86)..(112)
<223> OTHER INFORMATION: stem loop III (SL III)
<220> FEATURE:
<221> NAME/KEY: stem_loop
<222> LOCATION: (148)..(164)
<223> OTHER INFORMATION: stem loop IV (SL IV)

<400> SEQUENCE: 12
gagagagttg cacggctaag cactgcaata gaagggctct gcggcataaa atgagcctat    60
tctagggaga catgtcatct ttcaagaagg ttgagtgttc aagtgtcctt ccccaggaa    120 aaacaacacg ggaccagacc aggacccctc tgggtgatga gcctgggagg aggttatgtg   180
tacggctcct ttacctacac actggggatt tgacctctat ctccactctc atta          234

<210> SEQ ID NO 13
<211> LENGTH: 240
<212> TYPE: DNA
<213> ORGANISM: Mus musculus
<220> FEATURE:
<223> OTHER INFORMATION: RNA transport element (RTE) prototype family
      member GenBank Accession No. AL450331
<220> FEATURE:
<221> NAME/KEY: stem_loop
<222> LOCATION: (8)..(24)
<223> OTHER INFORMATION: stem loop I (SL I)
```

```
<220> FEATURE:
<221> NAME/KEY: stem_loop
<222> LOCATION: (28)..(65)
<223> OTHER INFORMATION: stem loop II (SL II)
<220> FEATURE:
<221> NAME/KEY: stem_loop
<222> LOCATION: (85)..(111)
<223> OTHER INFORMATION: stem loop III (SL III)
<220> FEATURE:
<221> NAME/KEY: stem_loop
<222> LOCATION: (147)..(170)
<223> OTHER INFORMATION: stem loop IV (SL IV)

<400> SEQUENCE: 13
gagagagttg cacggctaag cactgcaatg gaaaggctct gcggcatata tgagcctatt      60
ctagggagac atgtcatctt tcatgaaggt tcagtgtcct agttcccttc ccccaggcaa     120
aacgacacgg gagcaggtca gggttgctct gggtaaaagc ctgtgagcct aagagctaat    180
cctgtacatg gctcctttac ctacacactg gggatttgac ctctatctcc actctcatta   240
```